US007304046B2

(12) United States Patent
Borch et al.

(10) Patent No.: US 7,304,046 B2
(45) Date of Patent: Dec. 4, 2007

(54) PHOSPHORAMIDE COMPOUNDS

(75) Inventors: Richard F. Borch, Lafayette, IN (US); Marcy Hernick, West Lafayette, IN (US); Carolee Flader, Maple Grove, MN (US)

(73) Assignee: Purdue Research Foundation, West Lafayette, IN (US)

( * ) Notice: Subject to any disclaimer, the term of this patent is extended or adjusted under 35 U.S.C. 154(b) by 169 days.

(21) Appl. No.: 10/725,191

(22) Filed: Dec. 1, 2003

(65) Prior Publication Data

US 2004/0176332 A1 Sep. 9, 2004

Related U.S. Application Data

(63) Continuation of application No. 10/047,465, filed on Jan. 14, 2002, now Pat. No. 6,656,926, which is a continuation of application No. PCT/US00/19361, filed on Jul. 14, 2000.

(60) Provisional application No. 60/143,799, filed on Jul. 14, 1999.

(51) Int. Cl.
*A16K 31/661* (2006.01)
*C07F 9/22* (2006.01)

(52) U.S. Cl. ............... 514/138; 558/70; 558/199; 514/137

(58) Field of Classification Search ............... 558/70, 558/199; 514/137, 138
See application file for complete search history.

(56) References Cited

U.S. PATENT DOCUMENTS

| 4,908,356 | A | * | 3/1990 | Borch et al. ............ 514/90 |
| 5,190,929 | A | * | 3/1993 | Borch et al. ............ 514/80 |
| 5,233,031 | A | | 8/1993 | Borch et al. |
| 5,472,956 | A | | 12/1995 | Borch et al. ............ 514/95 |
| 5,659,061 | A | * | 8/1997 | Glazier ............ 558/166 |
| 6,656,926 | B2 | * | 12/2003 | Borch et al. ............ 514/80 |
| 6,903,081 | B2 | | 6/2005 | Borch et al. |

FOREIGN PATENT DOCUMENTS

| EP | 0553673 | 1/1993 |
| WO | WO-89/11484 | 11/1989 |
| WO | WO-90/10636 | 9/1990 |
| WO | WO 93/06120 | 4/1993 |
| WO | WO-96/33198 | 10/1996 |
| WO | WO 01/74827 | 10/2001 |

OTHER PUBLICATIONS

Flader, Carolee, et al., "Development of Novel Quinone Phosphorodiamidate Prodrugs Targeted to DT-Diaphorase", *J. Med. Chem.*, vol. 43, No. 16, (Aug. 10, 2000),3157-3167.
Workman, Paul, "Enzyme-Directed Bioreductive Drug Development Revisited: A commentary on recent progress and future prospects with emphasis on quinone anticancer agents and quinone metabolizing enzymes, particularly DT-diaphorase", *Oncol. Res.*, vol. 6, XP000946783, (1994),461-475.
"The Synthesis of O-Monosaccharldyl-Methoxycarbonyl-Phosphonamidaes by Arbuzov Reaction," Chen et al., *Chinese Chemical Letters*, vol. 6, No. 1, pp. 23-26, 1995.
"Design and Synthesis of Lipophillic Phosphoramidate d4T-MP Prodrugs Expressing High Potancy Against HIV In Cell Culture: Structural Determinants for *In vitro* Activity and OSAR," Sleeiqul, et al., *J. Med. Chem*.1999, 42, 4122-4128.
"Phosphoramidates as Potent Prodrugs of Anti-HIV Nucleotides: Studies In the Amino Region," McGuigan et al., *Antiviral Chemistry & Chemotherapy* (1996) 7(1), 31-36.
"Design and Synthesis of Noval Nucleotide Prodrugs," Meyers et al., American Association for Cancer Research 2000 (Abstract Proof Page), Abstract #100710, dated Dec. 2, 1999.
"Protein Tyrosine Kinases and Cancer,"Kollbaba et al., *Biochimica et Biophysics Acta* 1333 (1997) F217-F248.
"Receptor Protein-Tyrosine Kinases and Their signal Transduction Pathways," van der Geer et al., *Annu. Rev. Cell Biol.*, 1994, 10:251-337.
"Src Homology Region 2 Domains Direct Protein-Protein Interactions in Signal Transduction," Moran et al., *Proc. Natl. Acad. Sci. USA*, vol. 87, Nov. 1990, pp. 8622-8626.
"Binding of SH2 Domains of Phospholipasa Cryl, GAP, and Src to Activated Growth Factor Receptors," Anderson et al., *Science*, vol. 250, Nov. 16, 1990, 979-982.
"Oncogenes and Signal Transduction," Cantley et al., *Cell*, vol. 64, Jan. 25, 1991, 281-302.
"Recognition and Specificity In Protein Tyrosine Kinase-Mediated Signalling," Songyang et al., *TIBS* 20, Nov. 1995, 470-475.
"Targeting Signal Transduction in the Discovery of Antiproliferative Drugs," Saltiel et al., *Chemistry & Biology*, 1996, vol. 3, No. 11, 887-893.
"Peptide Inhibitors of src SH3-SH2-Phosphoprotein Interactions," Glimer et al., *The Journal of Biological Chemistry*, vol. 269, No. 50, Dec. 16, 1994, 31711-31719.
"Structure-Based Design of a Novel Series of Nonpeptide Ligands That Bind to the pp60$^{src}$ SH2 Domain," Lunney et al., *J. Am. Chem. Soc.* 1997, 119, 12471-12476.
"Design, Synthesis, and Cocrystal Structure of a Nonpeptide SrcSH2 Domain Ligand," Plummer et al., *J. Med. Chem.* 1997, 40, 3719-3725.

(Continued)

*Primary Examiner*—Golam M. M. Shameem
(74) *Attorney, Agent, or Firm*—Barnes & Thornburg LLP

(57) ABSTRACT

The invention provides a compound of formula I:

$$R^1 \diagdown O \diagdown \underset{\underset{NR_cR_d}{|}}{\overset{\overset{O}{\|}}{P}} - NR_aR_b \qquad (I)$$

wherein $R^1$, $R_a$, $R_b$, $R_c$, and $R_d$ have any of the values defined in the specification, as well as pharmaceutical compositions comprising such compounds or salts. The compounds are useful for treating cancer in animals.

22 Claims, 2 Drawing Sheets

OTHER PUBLICATIONS

"Inhibition of SH2 Domain/Phosphoprotein Association by a Nonhydrolyzable Phosphonopeptide," Domchek et al., Biochemistry 1992, 31, 9865-9870.

"Nonhydrolyzable Phosphotyrosyl Mimetics for the Preparation of Phosphatase-resistant SH2 Domain Inhibitors," Burke, Jr., et al., Biochemistry, 1994, 33, 6490-6494.

L-O-(2-Malonyl)tyrosine: A New Phosphyotyrosyl Mimetic for the Preparation of Src Homology 2 Domain Inhibitory Peptides, Ye et al., J. Med. Chem. 1995, 38, 4270-7275.

"Comformationally Constrained Phosphotyrosyl Mimetics Designed as Monomeric Src Homology 2 Domain Inhibitors," Burke Jr., et al., J. Med. Chem. 1995, 38, 1386-1396.

"4'-O-[2-(2-Fluoromalonyl)]-L-Tyrosine: A Phosphotyrosyl Mimic for the Preparation of Signal Transduction Inhibitory Peptides," Burke Jr., et al., J. Med. Chem. 1996, 39, 1021-1027.

"Phosphotyrosine-Containing Dipeptides as High-Affinity Ligands for the p56$^{ICK}$ SH2 Domain," Llinas-Brunet et al., J. Med. Chem. 1999, 42, 722-729.

"Acquisition of High-Affinity, SH2-Targeted Ligands via a Spatially Focused Library," Lee et al., J. Med. Chem. 1999, 42, 784-787.

"Ligands for the Tyrosine Kinase p56-$^{ICK-}$ SH2 Domain: Discovery of Potent Dipeptide Derivatives with Monocharged, Nonhydrolyzable Phosphate Replacements," Beaulieu et al., J. Med. Chem. 1999, 42, 1757-1766.

"Synthesis and Biological Evaluation of 5-Fluoro-2'-Deoxyuridine Phosphoramidate Analogs," Fries et al., J. Med. Chem., 1995, 38, 2672-2680.

"Synthesis and Biological Activity of Noval 5-Fluoro-2'-Deoxyuridine Phosphoramidate Prodrugs," Meyers et al., J. Med. Chem., 2000, 43, 4313-4318.

"Synthesis and Evaluation of Nitroheterocyclic Phosphoramidates as Hypoxia-Selective Alkylating Agents," Borch et al., J. Med. Chem., 2000, 43, 2258-2265.

Gibbs et al., Current Medicinal Chemistry, vol. 8, No. 12, Oct. 2001, pp. 1437-1465.

Borch et al., European Journal of Cancer. Supplement, Pergamon, Oxford, GB, vol. 2, No. 8, Sep. 2004, p. 176.

Weidong et al., American Chemical Society. Abstracts of Papers at the National Meeting, ACS, Washington, D.C., vol. 228, Part 1, Aug. 26, 2004, p. U930.

\* cited by examiner

Scheme 1: Activation of cyclophosphamide and alkylation by phosphoramide mustard 2

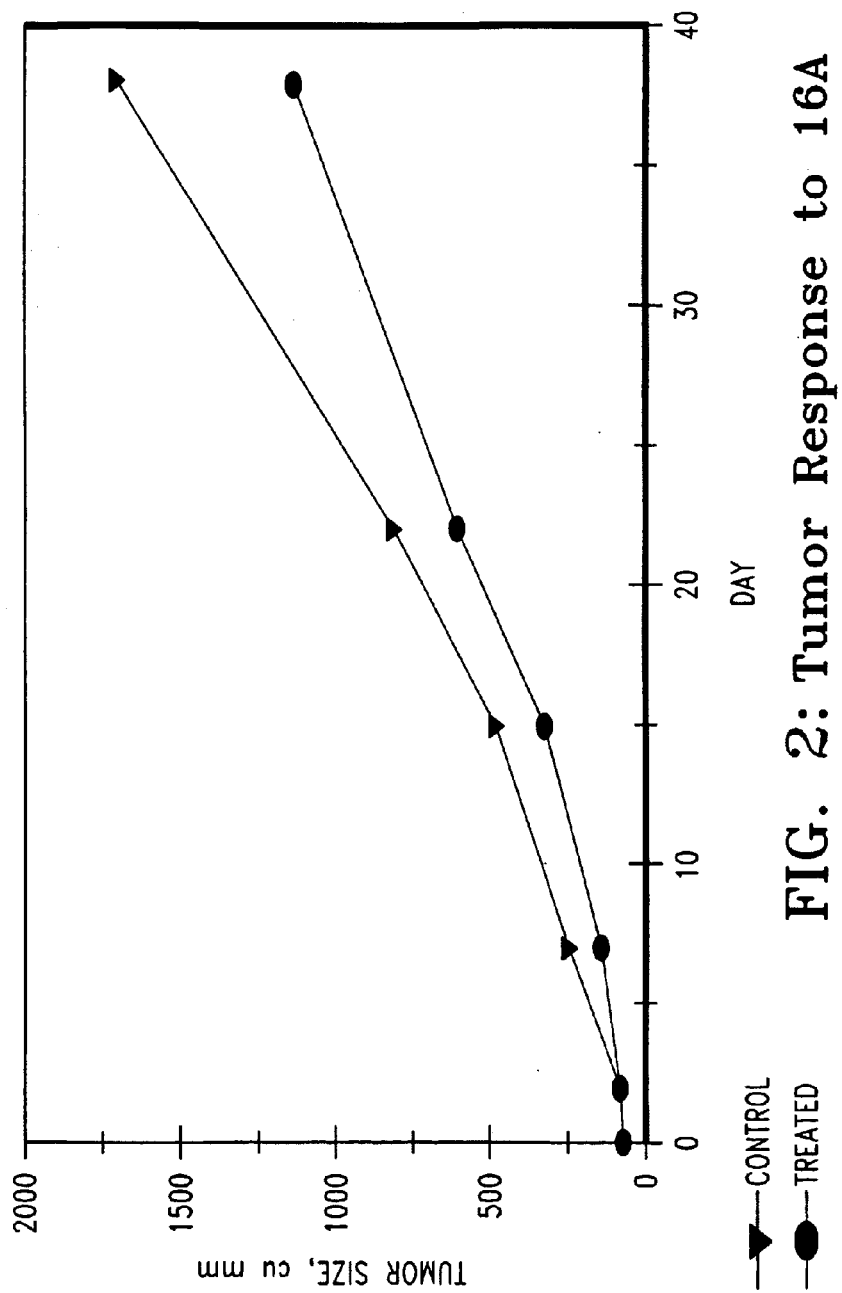
FIG. 2: Tumor Response to 16A

PHOSPHORAMIDE COMPOUNDS

RELATED APPLICATIONS

This application is a continuation under 37 C.F.R. 1.53(b) of U.S. application Ser. No. 10/047,465 filed Jan. 14, 2002, now U.S. Pat. No. 6,656,926 which is a continuation under 35 USC 111 (a) of International Application No. PCT/US00/19361 filed Jul. 14, 2000 and published in English as WO 01/04130 A1 on Jan. 18, 2001, which claims priority from U.S. Provisional application Ser. No. 60/143,799 filed Jul. 14, 1999, which applications and publication are incorporated herein by reference.

UNITED STATES GOVERNMENT FUNDING

The invention described herein was made with government support under Grant Number CA34619 awarded by the National Cancer Institute, and under Grant Number GM08298 awarded by the National Institutes of Health—National Institute of General Medical Sciences Predoctoral Training Grant in Chemical Pharmacology. The United States Government has certain rights in the invention.

BACKGROUND OF THE INVENTION

Increased selectivity of anti-cancer agents is an important factor in designing new drugs for the treatment of cancer. The design and synthesis of novel compounds that can be activated selectively in cancer cells is therefore an attractive way to target the inhibition of tumor growth. This strategy ensures that cytotoxicity occurs selectively in malignant cells and might lead to a reduction of many of the side effects commonly caused by chemotherapeutic agents currently in use. An approach to the enhancement of selectivity for cytotoxic chemotherapy involves the design of prodrugs that undergo preferential activation by enzymes that are overexpressed in tumors. These prodrugs, which are not cytotoxic until they are metabolically activated, can serve to deliver selectively the cytotoxic agent to the tumor site.

One such prodrug that is used clinically is the compound cyclophosphamide (1, FIG. 1). Cyclophosphamide is activated to 4-hydroxycyclophosphamide (1a) by hepatic cytochrome P-450 oxidation (FIG. 1). Subsequent β-elimination from the aldehyde tautomer of 1a releases phosphoramide mustard 2 as the active drug which can cyclize intramolecularly to a short-lived electrophilic aziridinium ion intermediate (3). Nucleophilic addition can then occur and the cyclization/addition process can be repeated. Ultimately, if DNA is the nucleophile, the phosphoramide mustard can cross-link DNA and inhibit further DNA replication, a process that leads to cell death.

The design of chemotherapeutic quinone prodrugs that are bioreductively activated by the enzyme DT-diaphorase has also been investigated (see for example P. Workman, *Oncol. Res.*, 1994, 6,461–475; and R. J. Riley and P. Workman, *Biochem. Pharmacol.*, 1992, 43, 1657–1669). Many of the compounds studied include benzimidazolequinone, benzoquinone and naphthoquinone prodrugs, with and without an alkylating moiety attached to the core ring structure, and indolequinone analogs patterned after the known cytotoxic agents Mitomycin C and E09. Sartorelli et al prepared a series of naphthoquinone prodrugs that could potentially be transformed into alkylating moieties following the expulsion of a leaving group from the bioreductively activated compound (see for example, N. E. Sladek, *Pharmac. Ther.*, 1988, 37, 301–355; and M. Colvin et al., *Cancer Res.*, 1976, 36, 1121–1126).

Despite the reported success in treating cancer with the compound Cyclophosphamide, there is currently a need for structurally novel therapeutic agents that can be used to treat cancer.

SUMMARY OF THE INVENTION

Applicant has discovered a series of novel compounds that possess useful cytotoxic properties when administered in vivo. Accordingly, the invention provides a compound of formula I:

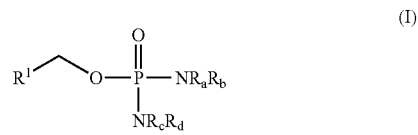

wherein:

$R^1$ is an organic releasing group comprising a quinone ring;

$R_a$, $R_b$, $R_c$, and $R_d$ are each independently hydrogen, $(C_1-C_6)$alkyl, or $-CH_2CH_2X$; and each X is independently halo, $(C_1-C_6)$alkylsulfonyl, halo$(C_1-C_6)$alkylsulfonyl, or arylsulfonyl, wherein each aryl is optionally substituted with one or more (e.g. 1, 2, 3, or 4) halo, $(C_1-C_6)$alkyl, halo$(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, or trifluoromethoxy;

provided at least two of $R_a$, $R_b$, $R_c$, and $R_d$ are $-CH_2CH_2X$;

or a pharmaceutically acceptable salt thereof.

The invention also provides a pharmaceutical composition comprising a compound of formula I, or a pharmaceutically acceptable salt thereof, in combination with a pharmaceutically acceptable diluent or carrier.

Additionally, the invention provides a therapeutic method for preventing or treating cancer (e.g. a tumor) comprising administering to a mammal in need of such therapy, an effective amount of a compound of formula I, or a pharmaceutically acceptable salt thereof.

The invention also provides a compound of formula I for use in medical therapy (preferably for use in treating cancer, such as a tumor) as well as the use of a compound of formula I for the manufacture of a medicament for the treatment of cancer (e.g. a tumor) in a mammal, such as a human.

The invention also provides processes and intermediates useful for preparing compounds of formula I, or salts thereof.

BRIEF DESCRIPTION OF THE FIGURES

FIG. 2 illustrates the response of the A498 human kidney carcinoma tumor to compound 16A.

DETAILED DESCRIPTION

Figure 1:
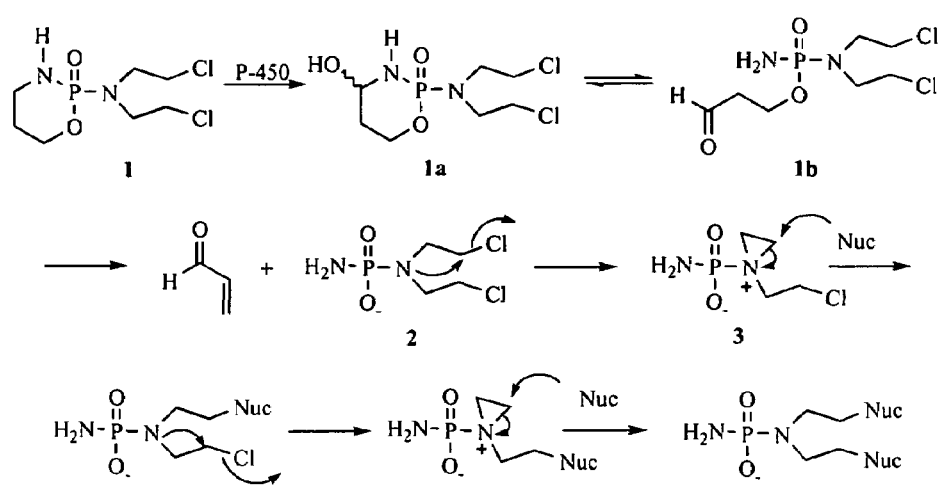
FIG. 1 illustrates the activation of cyclophosphamide in vivo.

The following definitions are used, unless otherwise described: halo is fluoro, chloro, bromo, or iodo. Alkyl, alkoxy, etc., denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

As used herein the term "organic releasing group comprising a quinone ring" includes mono-, bi- and poly-cyclic ring systems that comprise at least one quinone ring, which ring systems are capable of releasing a group of formula (V):

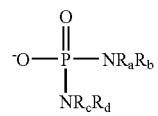

(V)

from a compound of formula I when the compound of formula I is administered to a mammal (e.g. a human). Preferred releasing groups include cyclic ring systems that can be reduced in vitro by the enzyme DT-diaphorase, leading to the release of the group of formula (V). Other preferred releasing groups include cyclic ring systems that can be substituted in vitro by glutathione (or other nucleophyles), leading to the release of the group of formula (V). A more preferred releasing groups is a group of formula II, III, or IV as described herein.

As used herein the term preventing or treating cancer includes killing cancer cells and/or inhibiting their growth or proliferation.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-cancer activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; and $(C_1-C_6)$alkanoyloxy can be formyloxy, acetoxy, propanoyloxy, butanoyloxy, isobutanoyloxy, pentanoyloxy, or hexanoyloxy.

A specific value for $R^1$ is a group of the formula (II):

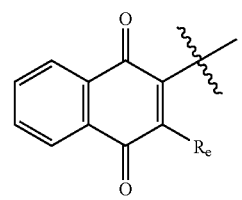

(II)

wherein $R_e$ is hydrogen, halo, $(C_1-C_6)$alkyl, halo$(C_1-C_6)$alkyl, $(C_1-C_6)$alkoxy, $(C_1-C_6)$alkanoyloxy, cyano, nitro, or $(C_1-C_6)$alkylthio; and wherein the benz ring is optionally substituted by one or more (e.g. 1, 2, 3, or 4) hydroxy, halo, $(C_1-C_6)$alkyl, halo$(C_1-C_6)$alkyl, $(C_1-C_6)$alkoxy, $(C_1-C_6)$alkylthio; $(C_1-C_6)$alkanoyl, $(C_1-C_6)$alkanoyloxy, $(C_1-C_6)$alkoxycarbonyl, cyano, nitro, mercapto, trifluoromethoxy, or $NR_fR_g$; wherein each $R_f$ and $R_g$ is independently hydrogen, $(C_1-C_6)$alkyl, $(C_1-C_6)$alkanoyl, phenyl, benzyl, or phenethyl; or $R_f$ and $R_g$ together with the nitrogen to which they are attached are pyrrolidino, piperidino or morpholino.

Another specific value for $R^1$ is a group of the formula (III):

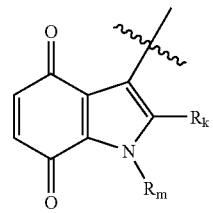

(III)

wherein $R_k$ is hydrogen or $(C_1-C_6)$alkyl; $R_m$ is hydrogen or $(C_1-C_6)$alkyl, phenyl, benzyl, or phenethyl; and wherein the benz ring is optionally substituted by one or two hydroxy, halo, $(C_1-C_6)$alkyl, halo$(C_1-C_6)$alkyl, $(C_1-C_6)$alkoxy, $(C_1-C_6)$alkylthio; $(C_1-C_6)$alkanoyl, $(C_1-C_6)$alkanoyloxy, $(C_1-C_6)$alkoxycarbonyl, cyano, nitro, mercapto, trifluoromethoxy, or $NR_fR_g$; wherein each $R_f$ and $R_g$ is independently hydrogen, $(C_1-C_6)$alkyl, $(C_1-C_6)$alkanoyl, phenyl, benzyl, or phenethyl; or $R_f$ and $R_g$ together with the nitrogen to which they are attached are pyrrolidino, piperidino or morpholino.

Another specific value for $R^1$ is a group of the formula (IV):

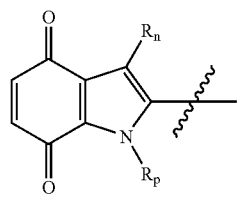

(IV)

wherein $R_n$ is hydrogen or $(C_1-C_6)$alkyl; $R_p$ is hydrogen or $(C_1-C_6)$alkyl, phenyl, benzyl, or phenethyl; and wherein the benz ring is optionally substituted by one or two hydroxy, halo, $(C_1-C_6)$alkyl, halo$(C_1-C_6)$alkyl, $(C_1-C_6)$alkoxy, $(C_1-C_6)$alkylthio; $(C_1-C_6)$alkanoyl, $(C_1-C_6)$alkanoyloxy, $(C_1-C_6)$alkoxycarbonyl, cyano, nitro, mercapto, trifluoromethoxy, or $NR_fR_g$; wherein each $R_f$ and $R_g$ is independently hydrogen, $(C_1-C_6)$alkyl, $(C_1-C_6)$alkanoyl, phenyl, benzyl, or phenethyl; or $R_f$ and $R_g$ together with the nitrogen to which they are attached are pyrrolidino, piperidino or morpholino.

A specific value for X is bromo, chloro, mesyl, trifluoromethylsulfonyl, or tosyl. A more specific value for X is bromo.

A specific value for $R_e$ is hydrogen, halo, methyl, or methylthio.

A specific value for $R_h$ is hydrogen or methyl.
A specific value for $R_k$ is hydrogen or methyl.
A specific value for $R_m$ is hydrogen or methyl.
A specific value for $R_n$ is hydrogen or methyl.
A specific value for $R_p$ is hydrogen or methyl.

A specific group of compounds of formula I are compounds wherein $R_a$ is $(C_1-C_6)$alkyl.

A specific group of compounds of formula I are compounds wherein $R_c$ is $(C_1-C_6)$alkyl.

A specific group of compounds of formula I are compounds wherein $R_a$ and $R_b$ are each independently —CH$_2$CH$_2$X.

A specific group of compounds of formula I are compounds wherein $R_c$, and $R_d$ are each independently —CH$_2$CH$_2$X.

A specific group of compounds of formula I are compounds wherein $R_b$ and $R_d$ are each independently —CH$_2$CH$_2$X.

A more specific group of compounds of formula I are compounds wherein $R_a$ is methyl.

A more specific group of compounds of formula I are compounds wherein $R_c$ is methyl.

A more specific group of compounds of formula I are compounds wherein $R_a$ and $R_b$ are each independently —CH$_2$CH$_2$Br.

A more specific group of compounds of formula I are compounds wherein $R_c$, and $R_d$ are each independently —CH$_2$CH$_2$Br.

A more specific group of compounds of formula I are compounds wherein $R_b$ and $R_d$ are each independently —CH$_2$CH$_2$Br.

A more specific group of compounds of formula I are compounds wherein $R_a$ and $R_b$ are each independently —CH$_2$CH$_2$Cl.

A more specific group of compounds of formula I are compounds wherein $R_c$, and $R_d$ are each independently —CH$_2$CH$_2$Cl.

A more specific group of compounds of formula I are compounds wherein $R_b$ and $R_d$ are each independently —CH$_2$CH$_2$Cl.

A preferred compound of the invention is:
2-(1,4-naphthoquinonyl)methyl N,N-bis(2-chloroethyl) phosphorodiamidate;
2-(3-Methyl-1,4-naphthoquinonyl)methyl N,N-bis(2-chloroethyl) phosphorodiamidate;
2-(3-Thiomethyl-1,4-naphthoquinonyl)methyl N,N-bis(2-chloroethyl) phosphorodiamidate;
2-(3-Bromo-1,4-naphthoquinonyl)methyl N,N-bis(2-chloroethyl) phosphorodiamidate;
2-(1,4-Naphthoquinonyl)methyl N,N-bis(2-bromoethyl) phosphorodiamidate;
2-(3-Methyl-1,4-naphthoquinonyl)methyl N,N-bis(2-bromoethyl) phosphorodiamidate;
2-(1,4-Naphthoquinonyl)methyl bis[N-(2-chloroethyl)] phosphorodiamidate;
2-(1,4-Naphthoquinonyl)methyl bis[N-methyl-N-(2-bromoethyl)]phosphorodiamidate;
2-(3-Methyl-1,4-naphthoquinonyl)methyl bis[N-methyl-N-(2-bromoethyl)] phosphorodiamidate;
2-(1,4-Naphthoquinonyl)methyl bis[N-methyl-N-(2-chloroethyl)] phosphorodiamidate;
3-(5-Methoxy-1-methyl-4,7-indolequinonyl)-methyl bis[N-methyl-N-(2-bromoethyl)]phosphorodiamidate;
3-(5-Methoxy-1-methyl-4,7-indolequinonyl)methyl N,N-bis(2-bromoethyl)-phosphorodiamidate;
2-(5-Methoxy-1-methyl-4,7-indolequinonyl)methyl bis[N-methyl-N-(2-bromoethyl)]phosphorodiamidate;
2-(5-Methoxy-1-methyl-4,7-indolequinonyl)methyl N,N-bis(2-chloroethyl)-phosphorodiamidate; or
2-(5-Methoxy-1-methyl-4,7-indolequinonyl)methyl N,N-bis(2-bromoethyl)-phosphorodiamidate;

or a pharmaceutically acceptable salt thereof.

A more prefered compound of the invention is:
3-(5-Methoxy-1-methyl-4,7-indolequinonyl)methyl N,N-bis(2-bromoethyl)-phosphorodiamidate;
2-(5-Methoxy-1-methyl-4,7-indolequinonyl)methyl bis[N-methyl-N-(2-bromoethyl)]phosphorodiamidate;
2-(5-Methoxy-1-methyl-4,7-indolequinonyl)methyl N,N-bis(2-chloroethyl)-phosphorodiamidate; or
2-(5-Methoxy-1-methyl-4,7-indolequinonyl)methyl N,N-bis(2-bromoethyl)-phosphorodiamidate;

or a pharmaceutically acceptable salt thereof.

Processes for preparing compounds of formula I are provided as further embodiments of the invention and are illustrated by the following procedures in which the meanings of the generic radicals are as given above unless otherwise qualified.

A compound of formula I wherein $R^1$ is a group of formula II can be prepared by oxidizing a corresponding compound wherein $R^1$ is a group of formula VI:

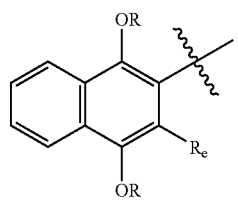

(VI)

wherein each R is independently $(C_1-C_6)$alkyl. The oxidation can be carried out under standard conditions, for example using ceric ammonium nitrate, Fremy's salt, or silver (II) oxide. Suitable conditions for carrying out such an oxidation are described in the Examples hereinbelow.

A compound of formula I wherein $R^1$ is a group of formula III can be prepared by oxidizing a corresponding compound wherein $R^1$ is a group of formula VII:

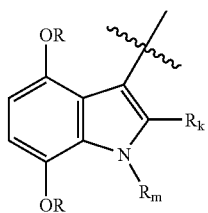

(VII)

wherein each R is independently $(C_1$–$C_6)$alkyl. The oxidation can be carried out under standard conditions, for example using ceric ammonium nitrate, Fremy's salt, or silver (II) oxide. Suitable conditions for carrying out such an oxidation are described in the Examples hereinbelow.

A compound of formula I wherein $R^1$ is a group of formula IV can be prepared by oxidizing a corresponding compound wherein $R^1$ is a group of formula VIII:

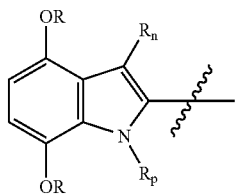

(VIII)

wherein each R is independently $(C_1$–$C_6)$alkyl. The oxidation can be carried out under standard conditions, for example using ceric ammonium nitrate, Fremy's salt, or silver (II) oxide. Suitable conditions for carrying out such an oxidation are described in the Examples hereinbelow.

An intermediate useful for preparing a compound of formula I is a corresponding compound of formula I wherein $R^1$ is a group of formula VI, VII, or VIII.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Determination of Releasing Group Activity

To determine whether representative compounds of formula I deliver the alkylating moiety (V) following quinone reduction, representative compounds of the invention were chemically reduced and the reaction was monitored by $^{31}$P NMR. The quinone was dissolved in CH$_3$CN (0.3 mL, or THF for 16a) and the activating agent (glutathione, or sodium dithionite) was dissolved in cacodylate buffer (0.4 mL, 0.4 M, pH 7.7). The buffer solution was added to the organic solution and the pH of the mixture was adjusted to ~7.4. The reaction mixture was transferred to a 5-mm NMR tube, and the data acquisition was started (pulse delay 30 μs). Spectra were taken every 2.5 minutes for 0.5 h, then every 5 min for 0.5 h, then every 10 min for 1 h, and time points for each spectrum were assigned from the initiation of the reaction. Chemical shifts are reported relative to the TPPO reference. The temperature of the probe was maintained at 37° C., if necessary, using the Bruker variable temperature unit. The relative concentrations of the intermediates were determined by measuring the peak areas.

Naphthoquinone 15a was reduced with sodium dithionite (3 equiv, 3:4 CH$_3$CN:0.4 M cacodylate buffer, pH~7.4, 37° C.), and the reaction was followed by $^{31}$P NMR. The resonance for quinone 3c at −5.3 ppm disappeared within 5 minutes and was replaced by the resonance for the corresponding phosphoramide mustard at −12.2 ppm. Similar results were obtained for compounds 16a, 17, and 40a.

Other Cellular Mechanisms of Quinone Activation

The Michael addition of sulfur nucleophiles to naphthoquinones is well known; and addition to the 3-position of the quinone might provide another pathway for phosphorodiamidate anion release. Two possible products could be predicted from the Michael addition of a nucleophile to the naphthoquinone. Addition at the 2-position leads to reversible formation of the kinetic product; and addition at the 3-position provides an intermediate that could expel the nucleophile in a reversible reaction, or could expel the phosphorodiamidate anion in an irreversible step. Experiments were carried out using sodium dimethyldithiocarbamate (DDTC), which contains a highly nucleophilic sulfur that is anionic at physiologic pH. Activation of 16a with DDTC (3 equiv, 3:4 THF:0.4 M cacodylate buffer, pH~7.3, RT) was monitored using $^{31}$P NMR. Three equivalents of nucleophile were used, assuming that one equivalent would be consumed by the Michael addition and the other two would be consumed by reaction with the resulting phosphorodiamidate anion. The resonance for quinone 16a (−5.7 ppm) disappeared and was replaced by the resonance for the phosphorodiamidate anion at −13.1 ppm within 5 min after addition of DDTC, confirming that nucleophilic activation of the naphthoquinone is rapid and complete.

The experiment above demonstrate that compound 16a is activated by a potent sulfur nucleophile. Thus, the following study was conducted to determine whether glutathione would activate compounds of formula I in a similar way.

Glutathione, the primary non-protein intracellular thiol, is responsible for maintaining the cellular redox environment and removing potential electrophilic cytotoxins. It is overproduced (1–10 mM intracellular concentrations) in many cancer cell lines, particularly those that have acquired resistance to anticancer drugs. Thus, the reaction of 15a with glutathione (3 equiv, 1:1.3 $CH_3CN$:0.4 M cacodylate buffer, pH~7.5, RT) was monitored by $^{31}P$ NMR. The reaction with glutathione was essentially identical to that of DDTC; the resonance for quinone 15a had disappeared and was replaced by the resonance for phosphorodiamidate anion within 4 minutes of glutathione addition. The result was essentially identical when only one equivalent of glutathione was used, again suggesting that activation of this compound is complete before cyclization of the phosphorodiamidate anion can occur.

The cytotoxic properties of a compound of the invention can be determined using in vitro pharmacological models which are well known to the art, or can be determined using Test A described below.

Test A: In Vitro Cytotoxicity (Clonogenic Survival of HT-29 and BE Cells):

The human colon carcinoma cell line HT-29 was obtained from the American Type Culture Collection (ATCC), and the BE cell line was provided by Dr. D. Ross, University of Colorado. A modification of the procedure described by Miribelli et al *Cancer Research*, 1985, 45, 32–39 was used to determine the clonogenic survival of the cells. HT-29 and BE cells in exponential growth were suspended in unsupplemented Eagles MEM medium (10 mL) at a final density of $1.7-2 \times 10^5$ cells/mL. Unsupplemented medium contains Minimum Essential Medium (Gibco) and HEPES (0.02 M). The drug stock solutions (0.1–40 mM) were prepared using either ethanol or dimethyl sulfoxide as solvent. The maximum amount of DMSO or ethanol used in the drug treatments was 1% of the total volume. Appropriate volumes (6.5 to 100 μL) of the drug stock solution were added to five vials of the cell suspensions, to give five different final drug concentrations, and 100 μL of solvent was added to a sixth vial for a control. The treated cells were incubated for 2 h (37° C., 5% $CO_2$). The cells were spun down and rinsed three times with supplemented medium (3 mL) and then diluted in 5 mL of supplemented medium. Supplemented medium is prepared by adding Fetal Bovine Serum (10%), gentamicin (0.05 mg/mL), L-glutamine (0.03 mg/mL), and sodium pyruvate (0.1 mM) to unsupplemented medium. The cells were counted using a Coulter Counter and then plated at 2–3 different densities for each drug concentration and incubated for 10 days. The colonies were stained with 0.5% crystal violet in 95% ethanol and those colonies comprised of 50 or more cells were counted using a microscope and pen-style counter. The $LC_{99}$ of each compound (the concentration at which there is a 1% cell survival) was determined by plotting the log surviving fraction vs. drug concentration. Data for representative compounds of the invention is provided in Table 1.

TABLE 1

| Compound | HT-29 $LC_{99}$ (μM) | BE $LC_{99}$ (μM) |
| --- | --- | --- |
| 15a | 11 | 13 |
| 15b | 2.1 | 1.0 |
| 15c | 4.2 | 5.9 |
| 15d | 4.1 | 3.3 |
| 16a | 7.8 | 4.6 |
| 16b | 1.7 | 1.2 |
| 17 | 14 | 7.8 |
| 40a | 4.5 | 1.2 |
| 40b | 1.5 | 0.44 |
| 40c | 4.5 | 2.8 |
| 47 | 0.07 | 0.14 |

The above data suggests that compounds of formula I wherein $R_a$ and/or $R_c$ are alkyl are unexpectedly more cytotoxic than the corresponding compounds wherein $R_a$ and $R_c$ are hydrogen. Thus, prefered compounds of the invention include compounds of formula I wherein $R_a$ and/or $R_c$ are alkyl.

The growth inhibitory properties of representative compounds of the invention were also determined by evaluating their growth inhibitory activity against a series of human tumor cell lines using a 72-h drug exposure. Cell counts were measured using the MTT assay. The results are summarized in Table 2.

TABLE 2

Growth inhibitory activity of compounds 1–6

| Cpd | $IC_{50}$, nM[a] | | | | | | | |
| --- | --- | --- | --- | --- | --- | --- | --- | --- |
| | IGROV | MDA231 | PC-3 | HT-29 | PaCa-2 | A498 | A549 | UMUC3 |
| 40a | 2048 | 3228 | 2559 | 5925 | 2303 | 4459 | 11181 | 9953 |
| 16a | 18932 | 14656 | 9193 | 15266 | 4417 | 15599 | 4583 | 2823 |
| 47 | 494 | 40 | 66 | 65 | 25 | 344 | 23 | 2 |
| 4 | | 194 | 649 | 241 | 215 | 998 | 398 | 10 |
| 5 | 7588 | 210 | 420 | 93 | 13 | 2650 | 260 | 14 |
| 6a | 1700 | 3500 | 170 | 340 | 6 | 862 | 203 | 22 |
| 6b | 1473 | 1628 | 195 | 61 | 35 | 199 | 9 | 1 |

[a]IGROV = ovarian, MDA231 = breast, PC-3 = prostate, HT-29 = colon, PaCa-2 = pancreas, A498 = kidney, A549 = lung, UMUC3 = bladder Several interesting conclusions are apparent from these data. Compounds 40a and 16a are moderately active ($IC_{50}$ in the low micromolar range) against all cell lines and show relatively little selectivity for tumor cells of different tissue types. Second, compounds 3, 5, 6a and 6b show significant selectivity and exceptional potency against PaCa-2 and UMUC3 cell lines, with $IC_{50}$ values in the low nanomolar range. These results are especially significant because pancreatic cancer and bladder cancer are difficult tumors to treat clinically. These tumors are poorly responsive to most existing anticancer drugs, and therapeutic options are very limited.

The cytotoxic properties of a compound of the invention can also be determined using in vivo pharmacological models which are well known to the art. For example, compound 16a was tested in a xenograft model. This assay consisted of injecting nude mice subcutaneously with human tumor cells. The tumors were allowed to grow until a measurable mass was present (22 days), and a single dose of 16a was administered subcutaneously. The tumor size was measured periodically and the growth inhibition of the tumor was determined. The A498$_2$LM cell line, a sub-line of the A498 human kidney carcinoma, was used for the xenograft assay. The A498$_2$LM sub-line, which has a high DT-diaphorase level (1010 nmol cytochrome c reduced/min/mg protein), was developed by implanting the A498 cell line in mice and collecting the lung metastases that formed from the original tumor. Compound 16a exhibited a 40% growth inhibition on Day 38 after a single dose of 25 mg/kg (FIG. 2).

The invention will now be illustrated by the following non-limiting Examples wherein unless otherwise noted the following general procedures were followed.

General Procedures $^1$H NMR spectra were measured on a 250 MHz Bruker NMR system equipped with a multinuclear ($^1$H, $^{13}$C, $^9$F and $^{31}$P) 5-mm probe. The NMR data acquisition/processing program MacNMR was used with the Tecmag data acquisition system. $^1$H Chemical shifts are reported in parts per million from tetramethylsilane. $^{31}$P NMR spectra were obtained on the same instrument using broadband gated decoupling. Chemical shifts are reported in parts per million from a coaxial insert containing 5% phosphoric acid in H$_2$O. All variable temperature experiments were conducted using a Bruker variable temperature unit.

Analtech precoated silica gel glass plates (250 microns) were used to perform thin layer chromatography. The plates were visualized using UV and/or one of the following two stains: 3% phosphomolybdic acid in methanol followed by heating or 1% 4-(p-nitrobenzyl)pyridine in acetone followed by heating and treatment with 3% KOH in acetone (to detect for an alkylating moiety). Chromatographic purifications were carried out by flash chromatography using silica gel grade 60 (230–400 mesh, 60 A). High performance liquid chromatography (HPLC) analyses were performed using a Beckman System Gold with a 126 Solvent Module, a 168 Detector set to either 250 or 280 nm and an Econosphere C18 5-micron column (250 mm, Alltech Associates). The mobile phase was acetonitrile: 0.1% trifluoroacetic acid in H$_2$O using the percentages indicated and a flow rate of 1 mL/min.

Elemental analyses were performed by the Purdue University Microanalysis Lab, West Lafayette, Ind. Mass spectral data was obtained from the Purdue University Mass Spectrometry Service, West Lafayette, Ind., using fast atom bombardment (FAB) with a 3-nitrobenzyl alcohol matrix.

A glass-calomel electrode on either a Radiometer pH meter or an Orion PerpHect LogR meter, model 330, was used for acidity measurements. Melting points were determined on a Mel-Temp II apparatus and are uncorrected. IR spectra were recorded on a Nicolet Magna IR 550 spectrometer using either a thin film or Nujol suspension, as noted, between NaCl plates. All anhydrous reactions were carried out in either a flame dried or oven dried flask under argon. Organic solutions were concentrated on a Buchi rotary evaporator.

Chemical reagents were purchased from Aldrich except NADH, NADPH, dicumarol and cytochrome c (Sigma) and ammonia (Matheson Gas). All cell culture reagents were purchased from Gibco Life Technologies. Purified human DT-diaphorase was supplied by Dr. S. Chen, City of Hope Medical Center, CA.

Tetrahydrofuran was distilled from sodium, with benzophenone ketyl as indicator, prior to use. Methylene chloride, diisopropylethylamine, triethylamine and acetonitrile were distilled from calcium hydride prior to use.

Butyllithium was purchased as a 2.5 M solution in hexanes, t-butyl hydroperoxide as a 5–6 M solution in decane, phosphorus trichloride as a 2 M solution in methylene chloride, lithium aluminum hydride as a 1.0 M solution in ether, sodium hydride as a 60% dispersion in mineral oil and lithium bis(trimethylsilyl)amide as a 1.0 M solution in tetrahydrofuran.

Schemes For Examples 1–4

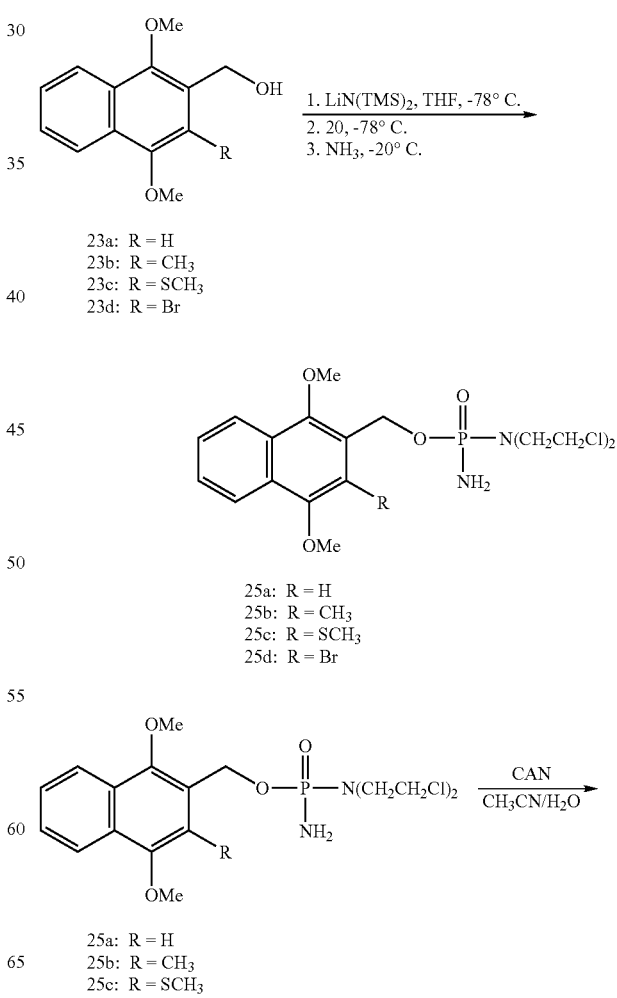

-continued

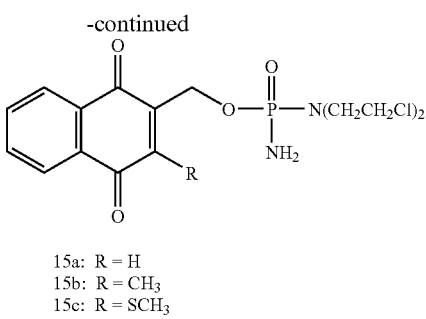

15a: R = H
15b: R = CH₃
15c: R = SCH₃

EXAMPLE 1

2-(1,4-Naphthoquinonyl)methyl N,N-bis(2-chloroethyl) phosphorodiamidate (15a)

Ceric ammonium nitrate (1.56 g, 2.85 mmol) in $H_2O$ (10 mL) was added in portions over 15 min to a solution of 25a (480 mg, 1.14 mmol) in acetonitrile (30 mL). The solution was stirred at room temperature for 1 h and extracted with $CHCl_3$ (3×). The combined organic layers were dried ($MgSO_4$), filtered and evaporated. Column chromatography of the crude product (6:94 MeOH:$CHCl_3$) afforded 15a (360 mg, 81%) as a yellow solid; $R_f$=0.45 (6:94 MeOH:$CHCl_3$); mp=105–107° C.; $^1$H NMR ($CDCl_3$): δ 8.09 (m, 2H), 7.77 (m, 2H), 7.03 (t, 1H), 5.05 (m, 2H, $J_{P-H}$=7.1 Hz), 3.68 (t, 4H), 3.54 (m, 4H), 3.01 (bs, 2H); $^{31}$P NMR ($CDCl_3$): δ 16.42 IR (Nujol): 1664, 1630, 1589 cm$^{-1}$. Anal. Calcd. for $C_{15}H_{17}Cl_2N_2O_4P$: C, 46.06; H, 4.38; N, 7.16. Found: C, 45.72; H, 4.17; N, 7.27.

The intermediate compound 25a was prepared as follows.
a. Methyl 1,4-dimethoxy-2-naphthoate (22)

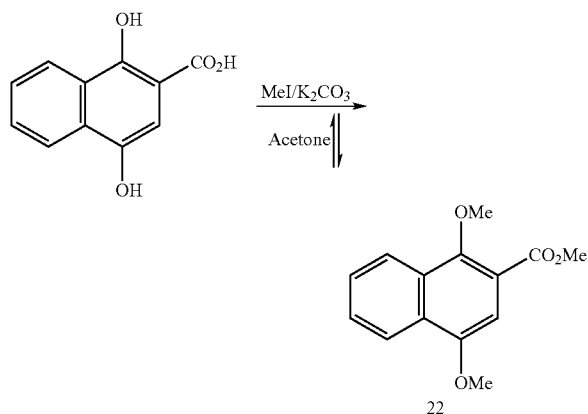

Potassium carbonate (30.50 g, 0.22 mol) and MeI (27.5 mL, 0.44 mol) were added to a solution of 1,4-dihydroxy-2-naphthoic acid (6.00 g, 0.029 mol) in acetone (120 mL) under argon. The mixture was refluxed for 48 h. Water (50 mL) was added and the mixture was extracted with $CH_2Cl_2$ (5×). The combined organic layers were washed with $H_2O$ (2×), dried ($MgSO_4$), filtered and evaporated. Column chromatography of the crude product (15:85 EtOAc:hexanes) afforded 22 (7.05 g, 97%) as a green solid; $R_f$=0.44 (15:85 EtOAc:hexanes); mp=48–50° C.; lit mp=52–55° C.[25] $^1$H NMR ($CDCl_3$): δ 8.24 (m, 2H), 7.59 (m, 2H), 7.16 (s, 1H), 4.02 (s, 3H), 4.01 (s, 3H), 4.00 (s, 3H).

b. 1,4-Dimethoxy-2-hydroxymethylnaphthalene (23a)

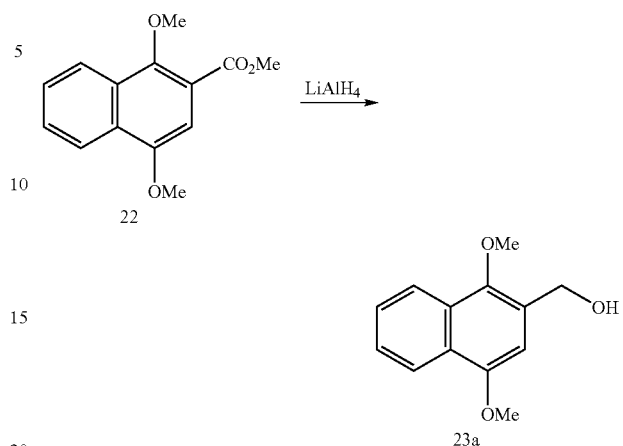

A solution of lithium aluminum hydride (29.2 mL, 29.2 mmol, 1 M in ether) in ether (30 mL) was heated to reflux under argon. A solution of ester 22 (7.18 g, 29.2 mmol) in ether (30 mL) and THF (8 mL) was added dropwise over 35 min via an addition funnel. The milky yellow mixture was refluxed for 3 h and then cooled to 0° C. Methanol (10 mL) was added dropwise and the resulting clear yellow solution was stirred for 1 h. Saturated $NH_4Cl$ (20 mL) and aqueous HCl (5 mL, 10%) were added and the mixture was extracted with ether (6×). The combined organic layers were washed with saturated $Na_2CO_3$ (2×) and $H_2O$ (2×), dried ($MgSO_4$), filtered and evaporated. Column chromatography of the crude product (35:65 EtOAc:hexanes) afforded 23a (5.82 g, 92%) as a pink solid; $R_f$=0.48 (35:65 EtOAc:hexanes); mp=69–70° C.; lit mp=68–70° C.[25]; $^1$H NMR ($CDCl_3$): δ 8.23 (dd, 1H), 8.03 (dd, 1H), 7.52 (m, 2H), 6.82 (s, 1H), 4.89 (s, 2H), 3.99 (s, 3H), 3.92 (s, 3H), 1.95 (bs, 1H).

c. 2-(1,4-Dimethoxynaphthyl)methyl N,N-bis(2-chloroethyl) phosphorodiamidate (25a). Lithium bis(trimethylsilyl)amide (2.50 mL, 2.50 mmol, 1.0 M in THF) was added dropwise via syringe to a solution of alcohol 23a (500 mg, 2.29 mmol) in THF (10 mL) at –78° C. under argon. The resulting solution was stirred for 5 min and added dropwise via syringe to a solution of bis(2-chloroethyl)phosphoramidic dichloride (20) (710 mg, 2.75 mmol) in THF (20 mL) at –78° C. The reaction mixture was stirred at –78° C. for 1.5 h and then was warmed to –20° C. Gaseous ammonia was passed through the reaction mixture for 10 min. The mixture was stirred for an additional 10 min, aqueous HCl (2%, 30 mL) was added and the mixture was extracted with EtOAc (4×). The combined organic layers were washed with saturated NaCl (2×), dried ($MgSO_4$), filtered and evaporated. Column chromatography of the crude product (2:98 MeOH:EtOAc) afforded 25a (480 mg, 50%) as a yellow oil; $R_f$=0.59 (2:98 MeOH:EtOAc); $^1$H NMR ($CDCl_3$): δ 8.25 (dd, 1H), 8.06 (dd, 1H), 7.54 (m, 2H), 6.85 (s, 1H), 5.33 (m, 2H, $J_{P-H}$=7.8 Hz), 4.01 (s, 3H), 3.94 (s, 3H), 3.65 (t, 4H), 3.48 (m, 4H), 2.77 (bs, 2H); $^{31}$P NMR ($CDCl_3$): δ 15.72.

EXAMPLE 2

2-(3-Methyl-1,4-naphthoquinonyl)methyl N,N-bis(2-chloroethyl) phosphorodiamidate (15b)

Compound 15b was prepared from 25b (440 mg, 1.01 mmol) as described above for 15a to give 289 mg (71%) of the product as a yellow solid after column chromatography (3:97 MeOH:CHCl$_3$); R$_f$=0.16 (3:97 MeOH:CHCl$_3$); mp=129–130° C.; $^1$H NMR (CDCl$_3$): δ 8.11 (m, 2H), 7.76 (m, 2H), 5.06 (m, 2H, J$_{P-H}$=7.3 Hz), 3.66 (t, 4H), 3.47 (dt, 4H), 3.02 (bs, 2H), 2.34 (s, 3H); $^{31}$P NMR (CDCl$_3$): δ 14.27; IR (Nujol): 1665, 1660, 1628, 1594 cm$^{-1}$. Anal. Calcd. for C$_{16}$H$_{19}$Cl$_2$N$_2$O$_4$P: C, 47.43; H, 4.73; N, 6.91. Found C, 47.59; H, 4.53; N, 6.84.

The intermediate compound 25b was prepared as follows.

a. 1,4-Dimethoxy-3-methyl-2-hydroxymethylnaphthalene (23b)

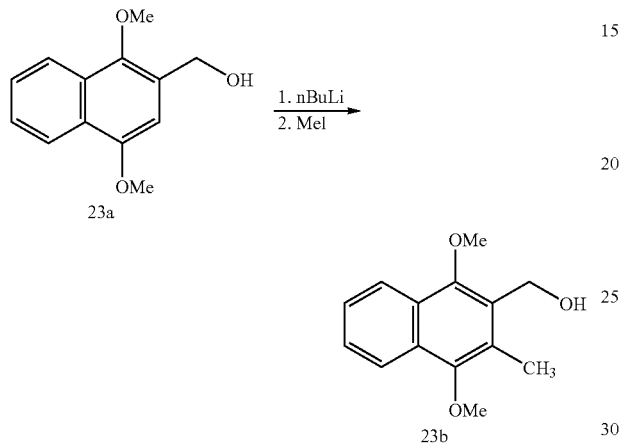

n-Butyllithium (7.3 mL, 18.3 mmol, 2.5 M in hexanes) was added dropwise via syringe to a solution of 23a (1.00 g, 4.58 mmol) in THF (30 mL) at −78° C. under argon. The solution was slowly warmed to room temperature and stirred for 1 h. Methyl iodide (0.34 mL, 5.50 mmol) was added dropwise and the solution was stirred for 20 min. Water (8 mL) was added and the mixture was extracted with EtOAc (4×). The combined organic layers were dried (MgSO$_4$), filtered and evaporated. Column chromatography of the crude product (45:55 EtOAc:hexanes) afforded 23b (0.61 g, 57%) as a yellow solid; R$_f$=0.59 (45:55 EtOAc:hexanes); mp=116–117° C.; lit mp=118–121,C$^{25}$; $^1$H NMR (CDCl$_3$): δ 8.07 (dd, 2H), 7.51 (m, 2H), 4.94 (s, 2H), 3.98 (s, 3H), 3.88 (s, 3H), 2.52 (s, 3H), 1.73 (bs, 1H).

b. 2-(3-Methyl-1,4-dimethoxynaphthyl)methyl N,N-bis(2-chloroethyl)phosphorodiamidate (25b). Compound 25b was prepared from 23b (500 mg, 2.15 mmol) as described above for 25a to give 440 mg (47%) of the product as a light yellow foam after column chromatography (1:99 MeOH:EtOAc); R$_f$=0.44 (1:99 MeOH:EtOAc); $^1$H NMR (CDCl$_3$): δ 8.08 (m, 2H), 7.53 (m, 2H), 5.31 (m, 2H, J$_{P-H}$=6.8 Hz), 3.98 (s, 3H), 3.89 (s, 3H), 3.64 (t, 4H), 3.45 (dt, 4H), 2.77 (bs, 2H), 2.52 (s, 3H); $^{31}$P NMR (CDCl$_3$): δ 15.65.

EXAMPLE 3

2-(3-Thiomethyl-1,4-naphthoquinonyl)methyl N,N-bis(2-chloroethyl)phosphorodiamidate (15c)

Compound 15c was prepared from 25c (134 mg, 0.287 mmol) as described above for 15a to give 72.0 mg (57%) of the product as a viscous orange oil after column chromatography (2:98 MeOH:CHCl$_3$); R$_f$=0.29 (2:98 MeOH: CHCl$_3$)

$^1$H NMR (CDCl$_3$): δ 8.10 (m, 2H), 7.75 (m, 2H), 5.21 (m, 2H, J$_{P-H}$=6.1 Hz), 3.66 (t, 4H), 3.46 (dt, 4H), 2.97 (bs, 2H), 2.74 (s, 3H); $^{31}$P NMR (CDCl$_3$): δ 15.25

IR (Nujol): 1666, 1643, 1588, 1542 cm$^{-1}$. Anal. Calcd. for C$_{16}$H$_{19}$Cl$_2$N$_2$O$_4$PS: C, 43.95; H. 4.38; N, 6.41. Found: C, 43.93; H, 4.21; N, 6.16.

The intermediate compound 25c was prepared as follows.

a. 1,4-Dimethoxy-3-thiomethyl-2-hydroxymethyl-naphthalene (23c)

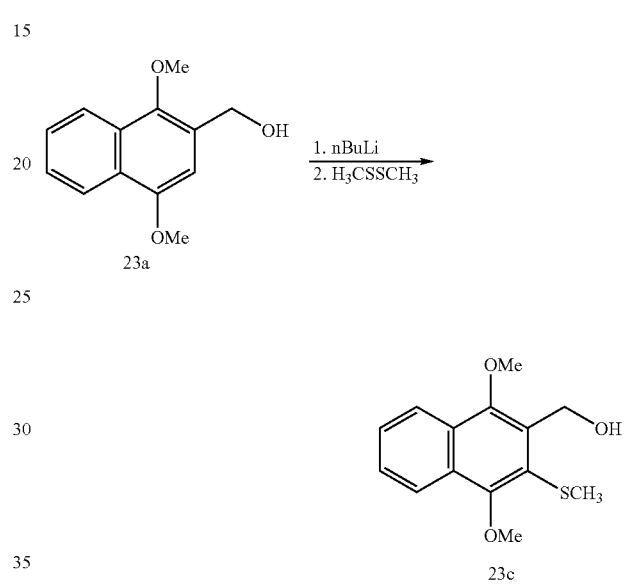

n-Butyllithium (0.73 mL, 1.83 mmol, 2.5 M in hexanes) was added dropwise to a solution of 23a (100 mg, 0.458 mmol) in THF (6 mL) at −78° C. under argon. The solution was slowly warmed to room temperature and stirred for 1 h. Dimethyl disulfide (0.050 mL, 0.55 mmol) was added dropwise. The clear, yellow solution became cloudy during the 30 min the reaction mixture was stirred. Water (1 mL) was added and the mixture was extracted with EtOAc (3×). The combined organic layers were washed with saturated NaCl, dried (MgSO$_4$), filtered and evaporated. Column chromatography of the crude product (20:80 EtOAc:hexanes) afforded 23c (71.2 mg, 59%, 82% based on recovered 23a, 28.0 mg) as a light green oil; R$_f$=0.26 (20:80 EtOAc:hexanes); $^1$H NMR (CDCl$_3$): δ 8.10 (m, 2H), 7.55 (m, 2H), 5.07 (s, 2H), 4.03 (s, 3H), 3.99 (s, 3H), 2.53 (s, 3H), 1.60 (bs, 1H).

b. 2-(3-Thiomethyl-1,4-dimethoxynaphthyl)methyl N,N-bis(2-chloro-ethyl) phosphorodiamidate (25c). Compound 25c was prepared from 23c (71.0 mg, 0.27 mmol) as described above for 25a to give 76.9 mg (61%) of the product as a yellow oil after column chromatography (EtOAc); R$_f$=0.22 (EtOAc); $^1$H NMR (CDCl$_3$): δ 8.12 (m, 2H), 7.57 (m, 2H), 5.48 (d, 2H, J=4.9 Hz), 4.04 (s, 3H), 4.00 (s, 3H), 3.64 (t, 4H), 3.49 (dt, 4H), 2.73 (bs, 2H), 2.51 (s, 3H); $^{31}$P NMR (CDCl$_3$): δ 14.62.

EXAMPLE 4

2-(3-Bromo-1,4-naphthoquinonyl)methyl N,N-bis(2-chloroethyl)phosphorodiamidate (15d)

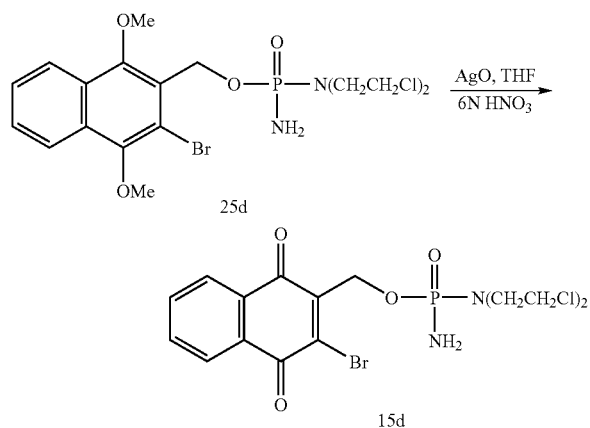

Silver (II) oxide (300 mg, 2.4 mmol) was added in one portion to a solution of 25d (200 mg, 0.40 mmol) in THF (15 mL) at room temperature. Nitric acid (6 N, 2 mL) was added to this suspension. The mixture was stirred for 20 min at room temperature, $H_2O$ (5 mL) was added and the mixture was extracted with $CHCl_3$ (3×). The combined organic layers were washed with saturated NaCl and $NaHCO_3$ (1 M), dried ($MgSO_4$), filtered and evaporated. Column chromatography of the crude product (2:98 MeOH:$CHCl_3$ until less polar impurities are removed, then 6:94 MeOH:$CHCl_3$) afforded 15d (156 mg, 83%) as a yellow solid; $R_f$=0.36 (6:94 MeOH:$CHCl_3$); mp=134–135° C.; $^1$H NMR ($CDCl_3$): δ 8.18 (m, 2H), 7.80 (m, 2H), 5.21 (m, 2H, $J_{P-H}$=6.5 Hz), 3.66 (t, 4H), 3.48 (dt, 4H), 2.97 (bs, 2H).
$^{31}$P NMR ($CDCl_3$): δ 15.32; IR (Nujol): 1680, 1675, 1659, 1605, 1589 cm$^{-1}$. Anal. Calcd. for $C_{15}H_{16}BrCl_2N_2O_4P$: C, 38.33; H, 3.43; N, 5.96. Found: C, 38.68; H, 3.42; N, 5.83.

The intermediate compound 25d was prepared as follows.

a. 1,4-Dimethoxy-3-bromo-2-hydroxyrmethylnaphthalene (23d)

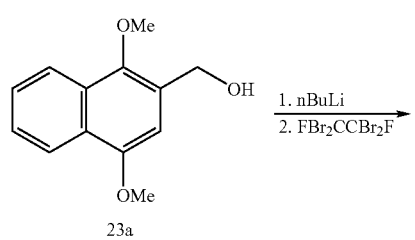

n-Butyllithium (2.9 mL, 7.33 mmol, 2.5 M in hexanes) was added dropwise to a solution of 23a (400 mg, 1.83 mmol) in THF (25 mL) at −78° C. under argon. The reaction mixture was slowly warmed to room temperature and stirred for 1 h. 1,2-dibromotetrafluoroethane (0.26 mL, 2.20 mmol) was added dropwise and the solution was stirred for 1 h. Water (10 mL) was added and the mixture was extracted with EtOAc (3×). The combined organic layers were dried ($MgSO_4$), filtered and evaporated. Column chromatography of the crude product (35:65 EtOAc:hexanes) afforded 23d (273 mg, 50%, 63% based on recovered 23a, 84 mg) as a yellow solid; $R_f$=0.62 (35:65 EtOAc:hexanes); mp=115–117° C.; $^1$H NMR ($CDCl_3$): δ 8.11 (m, 2H), 7.57 (m, 2H), 5.03 (s, 2H), 4.02 (s, 3H), 3.99 (s, 3H), 2.36 (bs, 1H).

b. 2-(3-Bromo-1,4-dimethoxynaphthyl)methyl N,N-bis(2-chloroethyl)-phosphorodiamidate (25d). Compound 25d was prepared from 23d (270 mg, 0.91 mmol) as described above for 25a to give 353 mg (78%) of the product as a white solid after column chromatography (EtOAc); $R_f$=0.17 (EtOAc); mp=112–1140C; $^1$H NMR ($CDCl_3$): δ 8.12 (m, 2H), 7.60 (m, 2H), 5.40 (m, 2H, $J_{P-H}$=5.9 Hz), 4.02 (s, 3H), 4.00 (s, 3H), 3.66 (t, 4H), 3.48 (dt, 4H), 2.82 (bs, 2H); $^{31}$P NMR ($CDCl_3$): δ 14.38.

Scheme for Examples 5 and 6

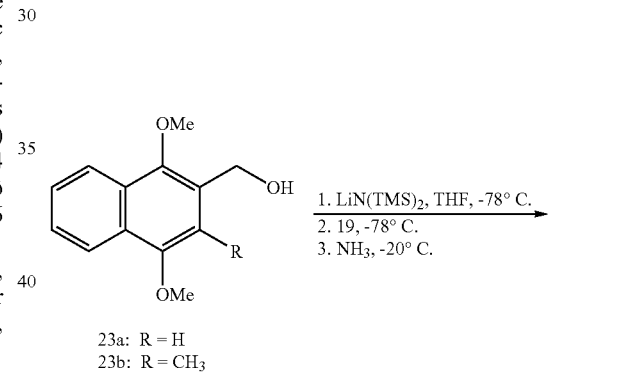

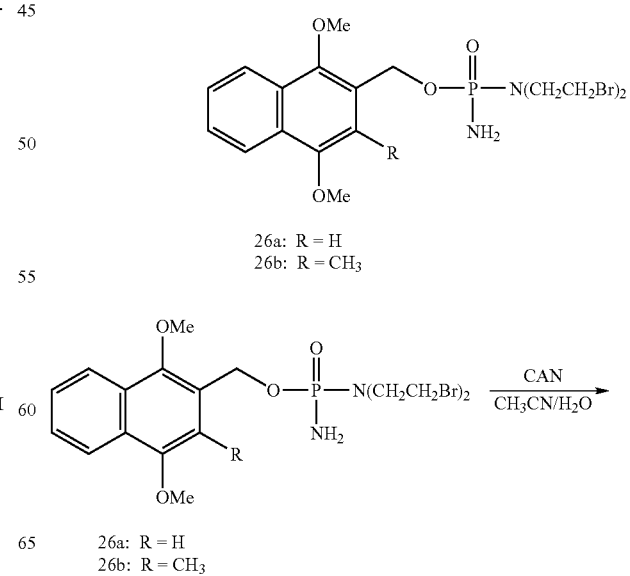

-continued

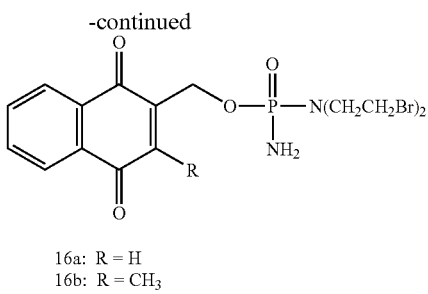

16a: R = H
16b: R = CH₃

EXAMPLE 5

2-(1,4-Naphthoquinonyl)methyl N,N-bis(2-bromoethyl) phosphorodiamidate (16a)

Ceric ammonium nitrate (1.83 g, 3.33 mmol) in $H_2O$ (15 mL) was added in portions over 15 min to a solution of 26a (680 mg, 1.33 mmol) in $CH_3CN$ (60 mL). The reaction was stirred at room temperature for 1 h and extracted with $CHCl_3$ (3×). The combined organic layers were dried ($MgSO_4$), filtered and evaporated. Column chromatography of the crude product (2:98 MeOH:EtOAc) afforded 16a (550 mg, 86%) as a yellow solid; $R_f$=0.51 (2:98 MeOH:EtOAc); mp=118–119° C.; $^1H$ NMR ($CDCl_3$): δ 8.10 (m, 2H), 7.77 (m, 2H), 7.03 (t, 1H), 5.05 (m, 2H, $J_{P-H}$=7.0 Hz), 3.55 (m, 8H), 2.98 (bs, 2H); $^{31}P$ NMR ($CDCl_3$): δ 16.18; IR (Nujol): 1664, 1627, 1591 cm$^{-1}$. Anal. Calcd. for $C_{15}H_{17}Br_2N_2O_4P$: C, 37.53; H, 3.57; N, 5.83. Found: C, 37.80; H, 3.57; N, 5.56.

The intermediate compound 19 was prepared as follows.
a. bis(2-Bromoethyl)amine hydrobromide (18Br)

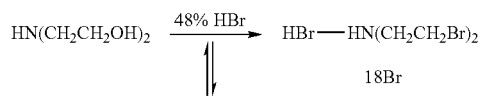

Hydrobromic acid (75 mL, 0.45 mol, 48% by wt) was added slowly, with stirring, to diethanolamine (11.0 g, 0.10 mol) at 0° C. The reaction mixture was heated to reflux and then distilled through a 14/20 vigreaux column. The distillate temperature was 100° C. for the first 15 mL collected and 125° C. for the remainder. After a total of 40 mL of distillate was collected, additional 48% HBr (50 mL, 0.30 mol) was added and 50 mL of distillate was collected. Hydrobromic acid (25 mL, 48%) was added and the reaction mixture was refluxed overnight. The reaction mixture was then distilled (~30 mL collected) and the still pot residue was poured into acetone at –78° C. The white solid that precipitated (10.3 g, 22% diethanolamine hydrobromide and 78% product 18Br as determined by $^1H$ NMR) was collected by filtration. This impure product can either be used directly in the subsequent phosphorylation reaction or can be purified by repeated recrystallization from acetone. This recrystallization procedure actually crystallizes out diethanolamine hydrobromide, so that purer product 18Br is recovered from the filtrate upon successive recrystallization attempts; $^1H$ NMR of 18Br ($D_2O$): δ 3.55 (t, 4H), 3.45 (t, 4H).

$^1H$ NMR of diethanolamine hydrobromide ($D_2O$): δ 3.78 (t, 4H), 3.12 (t, 4H).

b. bis(2-Bromoethyl)phosphoramidic dichloride (19):

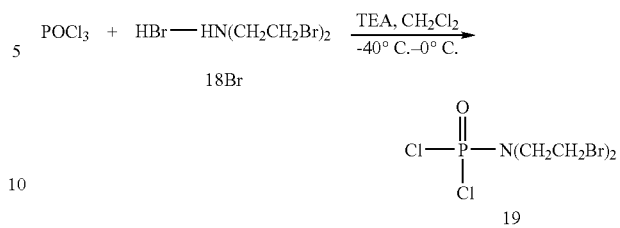

Phosphorus oxychloride (0.30 mL, 3.2 mmol) was added slowly to a suspension of hydrobromide salt 18Br (1.00 g, 3.2 mmol) in $CH_2Cl_2$ (22 mL) at –40° C. under argon. Triethylamine (1.20 mL, 8.6 mmol) was added dropwise via syringe over 5 min while the reaction mixture was vigorously stirred to avoid local heating. The cloudy white reaction mixture was warmed to 0° C. over 2.5 h and stirred at 0° C. for 4 h. Saturated ammonium chloride (8 mL) was added and the mixture was extracted with $CH_2Cl_2$ (3×). The combined organic layers were dried ($MgSO_4$), filtered and evaporated. Column chromatography of the crude product (20:80 EtOAc:hexanes) afforded 19 (0.76 g, 68%) as a white solid; $R_f$=0.56 (20:80 EtOAc:hexanes); mp=43–44° C.; lit mp=39–40° C.$^{25}$; $^1H$ NMR ($CDCl_3$): δ 3.73 (dt, 4H), 3.55 (t, 4H); $^{31}P$ NMR ($CDCl_3$): δ 16.48.

The intermediate compound 26a was prepared as follows.
c. 2-(1,4-Dimethoxynaphthyl)methyl N,N-bis(2-bromoethyl) phosphorodiamidate (26a). Lithium bis(trimethylsilyl)amide (6.05 mL, 6.05 mmol, 1 M in THF) was added dropwise via syringe to a solution of alcohol 23a (1.20 g, 5.50 mmol) in THF (20 mL) at –78°C under argon. The resulting solution was stirred for 5 min and then added dropwise to a solution of bis(2-bromoethyl)-phosphoramidic dichloride (19) (2.29 g, 6.60 mmol) in THF (50 mL) at –78° C. The reaction mixture was stirred at –78° C. for 1.5 h and then warmed to –20° C. Gaseous ammonia was passed through the reaction mixture for 10 min. The mixture was stirred for 10 min, aqueous HCl (2%, 70 mL) was added and the mixture was extracted with EtOAc (3×). The combined organic layers were washed with saturated NaCl (2×), dried ($MgSO_4$), filtered and evaporated. Column chromatography of the crude product (70:30 EtOAc:hexanes) afforded 26a (1.20 g, 43%) as a white solid; $R_f$=0.33 (70:30 EtOAc:hexanes); mp=112–113° C.; $^1H$ NMR ($CDCl_3$): δ 8.23 (dd, 1H), 8.06 (dd, 1H), 7.54 (m, 2H), 6.84 (s, 1H), 5.26 (m, 2H, $J_{P-H}$=8.1 Hz), 4.01 (s, 3H), 3.94 (s, 3H), 3.50 (m, 8H), 2.78 (bs, 2H); $^{31}P$ NMR ($CDCl_3$): δ 15.67.

EXAMPLE 6

2-(3-Methyl-1,4-naphthoquinonyl)methyl N,N-bis(2-bromoethyl) phosphorodiamidate (16b)

Compound 16b was prepared from 23b (470 mg, 0.897 mmol) as described above for 16a to give 230 mg (52%) of the product as a yellow solid after column chromatography (6:94 MeOH:$CHCl_3$); $R_f$=0.28 (6:94 MeOH:$CHCl_3$); mp=117–119° C.; $^1H$ NMR ($CDCl_3$): δ 8.12 (m, 2H), 7.76 (m, 2H), 5.06 (m, 2H, $J_{P-H}$=7.6 Hz), 3.50 (m, 8H), 3.02 (bs, 2H), 2.34 (s, 3H); $^{31}P$ NMR ($CDCl_3$): δ 15.72; IR (Nujol): 1662, 1626, 1594, 1568 cm$^{-1}$; HPLC (50:50 $CH_3CN$:0.1% TFA/$H_2O$): 4.78 min, 95.6%; FAB MS: Calcd. for $C_{16}H_{19}Br_2N_2O_4P$: (M+H)$^+$492.9527; Found 492.9542.

The intermediate compound 23b was prepared as follows.

a. 2-(3-Methyl-1,4-dimethoxynaphthyl)methyl N,N-bis(2-bromoethyl)phosphorodiamidate (26b). Compound 26b was prepared from 23b (480 mg, 2.07 mmol) as described above for 26a to give 480 mg (44%) of the product as a viscous yellow oil after column chromatography (2:98 MeOH:EtOAc); $R_f$=0.63 (2:98 MeOH:EtOAc); $^1$H NMR (CDCl$_3$): δ 8.09 (d, 2H), 7.41 (m, 2H), 5.31 (m, 2H, $J_{P-H}$=7.1 Hz), 3.98 (s, 3H), 3.89 (s, 3H), 3.48 (m, 8H), 2.77 (bs, 2H), 2.53 (s, 3H); $^{31}$P NMR (CDCl$_3$): δ 15.32.

EXAMPLE 7

2-(1,4-Naphthoquinonyl)methyl bis[N-(2-chloroethyl)] phosphorodiamidate (17)

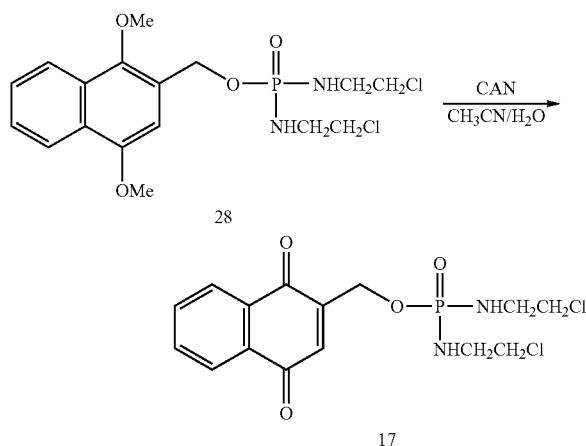

Ceric ammonium nitrate (0.20 g, 0.37 mmol) in H$_2$O (2 mL) was added in portions over 10 min to a solution of 28 (62.0 mg, 0.15 mmol) in CH$_3$CN (5 mL). The solution was stirred at room temperature for 1 h. Water (3 mL) was added and the mixture was extracted with CHCl$_3$ (3×). The combined organic layers were dried (MgSO$_4$), filtered and evaporated. Column chromatography of the crude product (78:22 CHCl$_3$:Acetone until less polar impurities are removed, then 67:33 CHCl$_3$:Acetone) afforded 17 (42.4 mg, 74%) as a yellow solid; $R_f$=0.24 (67:33 CHCl$_3$:Acetone); mp=109–110° C.; $^1$H NMR (CDCl$_3$): δ 8.10 (m, 2H), 7.77 (m, 2H), 7.03 (t, 1H, J=1.9 Hz), 5.04 (dd, 2H, J=1.9 and 6.8 Hz), 3.65 (t, 4H), 3.36 (dt, 4H), 3.20 (bs, 2H); $^{31}$P NMR (CDCl$_3$): δ 14.83; IR (Nujol): 1662, 1633, 1594 cm$^{-1}$. Anal. Calcd. for C$_{15}$H$_{17}$Cl$_2$N$_2$O$_4$P: C, 46.06; H, 4.38; N, 7.16. Found: C, 46.04; H, 4.08; N, 6.78.

The intermediate compound 28 was prepared as follows.

a. 2-(1,4-Dimethoxynaphthyl)methyl bis[N-(2-chloroethyl)] phosphorodiamidate (28):

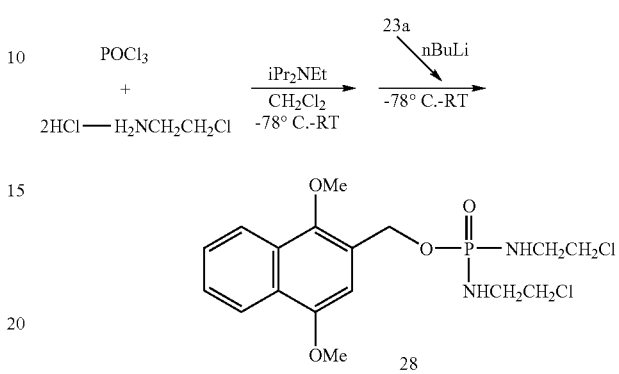

Phosphorus oxychloride (0.043 mL, 0.46 mmol) was added to a suspension of N-(2-chloroethyl)amine hydrochloride (112 mg, 0.96 mmol) in CH$_2$Cl$_2$ (10 mL) at −78° C. under argon. Diisopropylethylamine (0.34 mL, 1.92 mmol) was added dropwise and the reaction mixture was warmed to room temperature over 2 h and stirred for 7 h. After the phosphorylation reaction was completed, n-butyllithium (0.18 mL, 0.46 mmol, 2.5 M in hexanes) was added to a solution of alcohol 23a (100 mg, 0.46 mmol) in CH$_2$Cl$_2$ (5 mL) in a second flask at −78° C. under argon. The resulting solution was stirred for 15 min. The contents of the flask containing the phosphorylating reagent were added via syringe to the second solution with vigorous stirring at −78° C. The reaction mixture was slowly warmed to room temperature, stirred overnight, and then concentrated under reduced pressure until the volume was reduced to a third. The salts were separated and the crude product was purified by column chromatography (78:22 CHCl$_3$:Acetone until less polar impurities are removed, then 67:33 CHCl$_3$:Acetone) to afford 28 (62.0 mg, 32%, 87% based on recovered 23a, 63.0 mg) as a light yellow oil; $R_f$=0.31 (78:22 CHCl$_3$:Acetone); $^1$H NMR (CDCl$_3$): δ 8.24 (dd, 1H), 8.06 (dd, 1H), 7.55 (m, 2H), 6.84 (s, 1H), 5.25 (d, 2H, J=7.9 Hz), 4.01 (s, 3H), 3.94 (s, 3H), 3.59 (t, 4H), 3.28 (dt, 4H), 3.04 (bs, 2H); $^{31}$P NMR (CDCl$_3$): δ 14.72.

Scheme For Examples 8–10

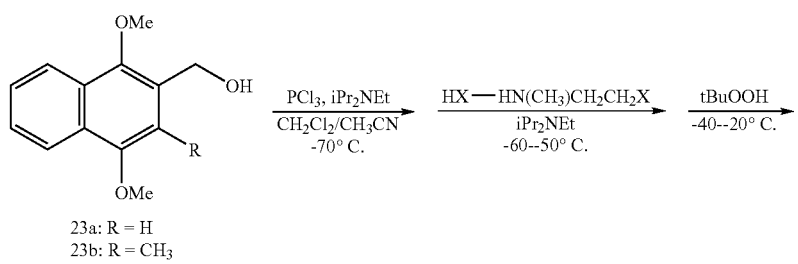

23a: R = H
23b: R = CH$_3$

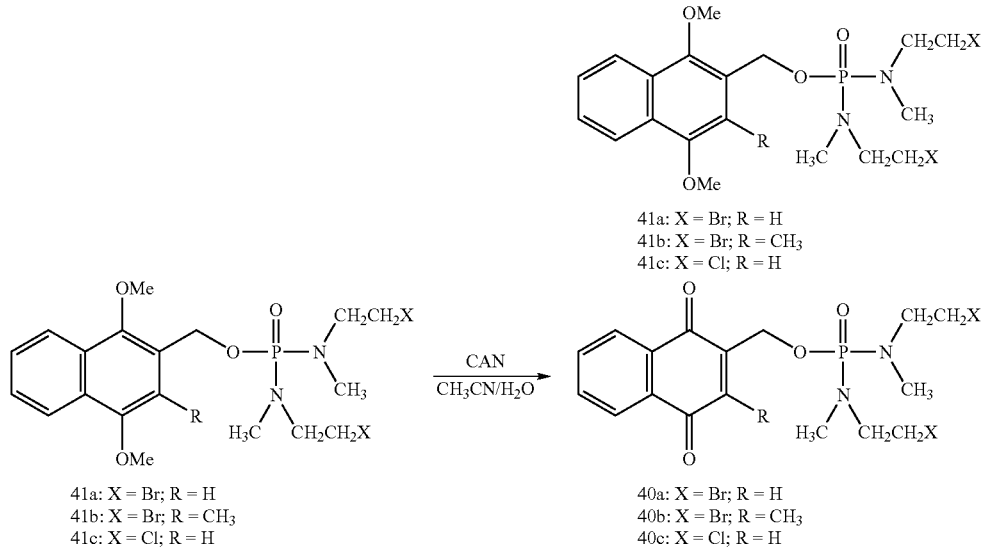

41a: X = Br; R = H
41b: X = Br; R = CH$_3$
41c: X = Cl; R = H

40a: X = Br; R = H
40b: X = Br; R = CH$_3$
40c: X = Cl; R = H

EXAMPLE 8

2-(1,4-Naphthoquinonyl)methyl bis[N-methyl-N-(2-bromoethyl)]phosphorodiamidate (40a)

Ceric ammonium nitrate (510 mg, 0.93 mmol) in H$_2$O (5 mL) was added in portions over 10 min to a solution of 41a (200 mg, 0.372 mmol) in CH$_3$CN (17 mL). The solution was stirred at room temperature for 1 h and extracted with CHCl$_3$ (3×). The combined organic layers were washed with H$_2$O and saturated NaCl, dried (MgSO$_4$), filtered and evaporated. Column chromatography of the crude product (2:98 MeOH:CH$_2$Cl$_2$) afforded 40a (164 mg, 87%) as a viscous brown oil; R$_f$=0.16 (2:98 MeOH:CH$_2$Cl$_2$); $^1$H NMR (CDCl$_3$): δ 8.10 (m, 2H), 7.77 (m, 2H), 7.03 (t, 1H, J=2.0 Hz), 5.04 (dd, 2H, J=2.0 and 6.4 Hz), 3.49 (m, 8H), 2.78 (d, 6H, J=9.7 Hz); $^{31}$P NMR (CDCl$_3$): δ 18.00; IR (neat): 1664, 1632, 1595 cm$^{-1}$.
Anal. Calcd. for C$_{17}$H$_{21}$Br$_2$N$_2$O$_4$P: C, 40.18; H, 4.17; N, 5.51. Found: C, 40.36; H, 4.09; N, 5.18.

The intermediate compound 41a was prepared as follows.
a. 2-(1,4-Dimethoxynaphthyl)methyl bis[N-methyl-N-(2-bromoethyl)] phosphorodiamidate (41a). A solution of alcohol 23a (100 mg, 0.46 mmol) in CH$_2$Cl$_2$ (2 mL) and CH$_3$CN (2 mL) was cooled to −70° C. and stirred under argon. Phosphorus trichloride (0.23 mL, 0.46 mmol, 2 M in CH$_2$Cl$_2$) was added dropwise followed by the dropwise addition of diisopropylethylamine (0.08 mL, 0.46 mmol). The reaction mixture was stirred for 25 min at −70° C. A solution of N-methyl-N-(2-bromoethyl)amine hydrobromide (200 mg, 0.92 mmol) in CH$_3$CN (2.5 mL) was added slowly via syringe, followed by additional diisopropylethylamine (0.32 mL, 1.84 mmol). The temperature was raised to −60 to −50° C. and the reaction was stirred for 1.25 h. t-Butyl hydroperoxide (1.1 mL, 5–6 M in decane) was added and the reaction mixture was warmed to −40 to −20° C. and stirred for 30 min. Water (3 mL) was added and the mixture was warmed to room temperature and extracted with CH$_2$Cl$_2$ (4×). The combined organic layers were washed with H$_2$O and saturated NaCl, dried (MgSO$_4$), filtered and evaporated. Column chromatography of the crude product (2:98 MeOH:EtOAc) afforded 41a (190 mg, 77%) as a light yellow oil; R$_f$=0.33 (2:98 MeOH:EtOAc); $^1$H NMR (CDCl$_3$): δ 8.24 (dd, 1H), 8.06 (dd, 1H), 7.54 (m, 2H), 6.87 (s, 1H), 5.24 (d, 2H, J=7.4 Hz), 4.01 (s, 3H), 3.93 (s, 3H), 3.43 (m, 8H), 2.71 (d, 6H, J=9.7 Hz); $^{31}$P NMR (CDCl$_3$): δ 17.60.

EXAMPLE 9

2-(3-Methyl-1,4-naphthoquinonyl)methyl bis[N-methyl-N-(2-bromoethyl)] phosphorodiamidate (40b)

Compound 40b was prepared from 41b (130 mg, 0.235 mmol) as described above for 40a to give 99 mg (81%) of the product as a yellow oil after column chromatography (3:97 MeOH:CH$_2$Cl$_2$); R$_f$=0.20 (3:97 MeOH:CH$_2$Cl$_2$); $^1$H NMR (CDCl$_3$): δ 8.12 (m, 2H), 7.75 (m, 2H), 5.04 (d, 2H, J=6.4 Hz), 3.43 (m, 8H), 2.71 (d, 6H, J=9.7 Hz), 2.35 (s, 3H); $^{31}$P NMR (CDCl$_3$): δ 17.77; IR (neat): 1663, 1626, 1595 cm$^{-1}$. Anal. Calcd. for C$_{18}$H$_{23}$Br$_2$N$_2$O$_4$P: C, 41.40; H, 4.44; N, 5.36. Found: C, 41.31; H, 4.28; N, 5.13.

The intermediate compound 41b was prepared as follows.
a. 2-(3-Methyl-1,4-dimethoxynaphthyl)methyl bis[N-methyl-N-(2-bromoethyl)] phosphorodiamidate (41b). Compound 41b was prepared from alcohol 23b (100 mg, 0.431 mmol) and N-methyl-N-(2-bromoethyl)amine hydrobromide as described above for 41a to give 135 mg (57%) of the product as a yellow oil after column chromatography (2:98 MeOH:EtOAc); R$_f$=0.37 (2:98 MeOH:EtOAc); $^1$H NMR (CDCl$_3$): δ 8.09 (dd, 2H), 7.52 (m, 2H), 5.28 (d, 2H, J=5.8 Hz), 3.97 (s, 3H), 3.89 (s, 3H), 3.41 (m, 8H), 2.67 (d, 6H, J=9.7 Hz), 2.53 (s, 3H); $^{31}$P NMR (CDCl$_3$): δ 17.28.

EXAMPLE 10

2-(1,4-Naphthoquinonyl)methyl bis[N-methyl-N-(2-chloroethyl)]phosphorodiamidate (40c)

Compound 40c was prepared from 41c (130 mg, 0.289 mmol) as described above for 40a to give 105 mg (87%) of the product as a brown oil after column chromatography (2:98 MeOH:EtOAc); R$_f$=0.55 (2:98 MeOH:EtOAc); $^1$H NMR (CDCl$_3$): δ 8.10 (m, 2H), 7.77 (m, 2H), 7.03 (t, 1H, J=2.0), 5.03 (dd, 2H, J=2.0 and 6.4 Hz), 3.66 (t, 4H), 3.42

(m, 4H), 2.78 (d, 6H, J=9.9 Hz); $^{31}$P NMR (CDCl$_3$): δ 18.21 ppm; IR (neat): 1664, 1633, 1595 cm$^{-1}$. Anal. Calcd. for C$_{17}$H$_{21}$Cl$_2$N$_2$O$_4$P: C, 48.70; H, 5.05; N, 6.68. Found: C, 48.36; H, 5.02; N, 6.35.

The intermediate compound 41c was prepared as follows.

a. 2-(1,4-Dimethoxynaphthyl)methyl bis[N-methyl-N-(2-chloroethyl)]phosphorodiamidate (41c). Compound 41c was prepared from alcohol 23a (100 mg, 0.458 mmol) and N-methyl-N-(2-chloroethyl)amine hydrochloride as described above for 41a to give 132 mg (64%) of the product as a light yellow oil after column chromatography (2:98 MeOH:EtOAc); R$_f$=0.33 (2:98 MeOH:EtOAc); $^1$H NMR (CDCl$_3$): δ 8.24 (dd, 1H), 8.06 (dd, 1H), 7.54 (m, 2H), 6.88 (s, 1H), 5.24 (d, 2H, J=7.3 Hz), 4.00 (s, 3H), 3.93 (s, 3H), 3.63 (t, 4H), 3.37 (dt, 4H), 2.72 (d, 6H, J=9.6 Hz); $^{31}$P NMR (CDCl$_3$): δ 17.91.

EXAMPLE 11

3-(5-Methoxy-1-methyl-4,7-indolequinonyl)-methyl bis[N-methyl-N-(2-bromoethyl)] phosphorodiamidate (47)

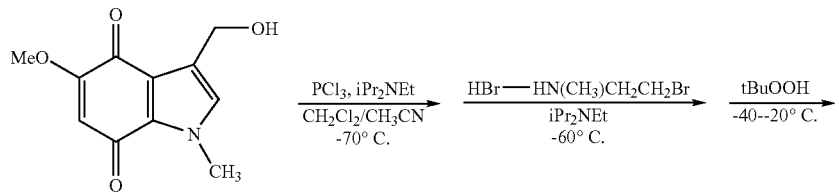

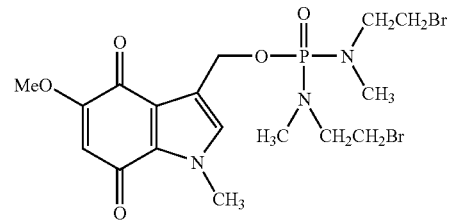

A solution of alcohol 42 (50 mg, 0.23 mmol) in CH$_2$Cl$_2$ (3 mL) and CH$_3$CN (2 mL) was cooled to −70° C. and stirred under argon. Phosphorus trichloride (0.115 mL, 0.23 mmol, 2 M in CH$_2$Cl$_2$) was added dropwise followed by the dropwise addition of diisopropylethylamine (0.04 mL, 0.23 mmol). The solution was stirred for 15 min and N-methyl-N-(2-bromoethyl)amine hydrobromide (99 mg, 0.46 mmol) in CH$_3$CN (1.5 mL) was added slowly via syringe followed by the dropwise addition of diisopropylethylamine (0.16 mL, 0.92 mmol). The mixture was stirred for 2 h below −60° C. t-Butyl hydroperoxide (0.23 mL, 5–6 M in decane) was added and the solution was warmed to −40 to −20° C. and stirred for 1 hr. Water (3 mL) was added and the mixture was extracted with CH$_2$Cl$_2$ (4×). The combined organic layers were washed with H$_2$O and saturated NaCl, dried (MgSO$_4$), filtered and evaporated. Column chromatography of the crude product (10:90 EtOH:ether) afforded 47 (25 mg, 20%) as an orange oil; R$_f$=0.48 (10:90 EtOH:ether); $^1$H NMR (CDCl$_3$): δ 6.91 (s, 1H), 5.68 (s, 1H), 5.14 (d, 2H, J=7.5 Hz), 3.96 (s, 3H), 3.83 (s, 3H), 3.42 (m, 8H), 2.72 (d, 6H, J=9.7 Hz); $^{31}$P NMR (CDCl$_3$): δ 16.51; IR (neat): 1673, 1643, 1597, 1511 cm$^{-1}$; HPLC (40:60 CH$_3$CN:0.1% TFA/H$_2$O): 8.78 min, 95.9%; FAB MS: Calcd. for C$_{17}$H$_{24}$Br$_2$N$_3$O$_5$P: (M+H)+539.9900; Found: 539.9901.

The intermediate compound 42 was prepared as follows.

a. 5-Methoxy-1-methylindole-3-carboxaldehyde (43)

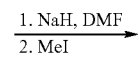

-continued

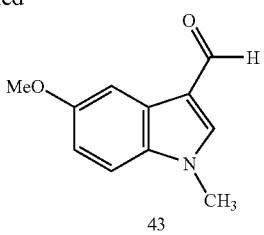

5-Methoxyindole-3-carboxaldehyde (300 mg, 1.71 mmol) was added in portions over 5 min to a suspension of sodium hydride (82 mg, 2.05 mmol, 60% dispersion in mineral oil) in DMF (8 mL) stirring under argon. The mixture was stirred for 30 min, methyl iodide (0.13 mL, 2.05 mmol) was added and the mixture was stirred for 1 h. Sodium bicarbonate (10%, 40 mL) was added and the mixture was extracted with EtOAc (4×). The combined organic layers were washed with sodium bicarbonate (10%, 2×) and saturated NaCl, dried (MgSO$_4$), filtered and evaporated. Column chromatography of the crude product (50:50 EtOAc:hexanes) afforded 43 (320 mg, 99%) as a light yellow solid; R$_f$=0.35 (50:50 EtOAc:hexanes); mp=130–1320C; lit mp=132–133° C.[53]; $^1$H NMR (CDCl$_3$): δ 9.95 (s, 1H), 7.79 (d, 1H, J=2.4 Hz), 7.62 (s, 1H), 7.25 (d, J=8.8 Hz), 6.96 (dd, 1H, J=2.4 and 8.9 Hz), 3.90 (s, 3H), 3.85 (s, 3H).

b. 5-Methoxy-1-methyl-4-nitroindole-3-carboxaldehyde (44)

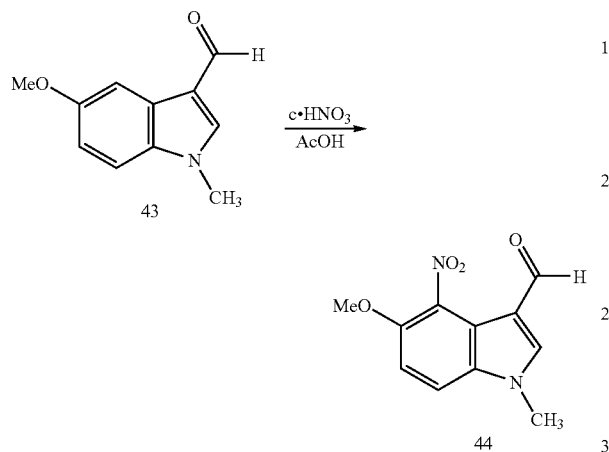

A mixture of concentrated HNO$_3$ (2 mL) in AcOH (11 mL) was added dropwise over 40 min to a solution of 43 (1.08 g, 5.71 mmol) in AcOH (70 mL) at 0° C. The mixture was warmed to room temperature, stirred overnight, and poured over ice. The product (44) was collected by filtration, washed with H$_2$O, and dried to give 1.18 g (88%) of a yellow solid; R$_f$=0.49 (EtOAc); mp=195–197° C.; lit mp=197–198° C.[53]; $^1$H NMR (CDCl$_3$): δ 9.84 (s, 1H), 7.83 (s, 1H), 7.45 (d, 1H, J=9.0 Hz), 7.11 (d, 1H, J=9.1 Hz), 3.96 (s, 3H), 3.90 (s, 3H).

c. 4-amino-5-methoxy-1 methylindole-3-carboxaldehyde (45)

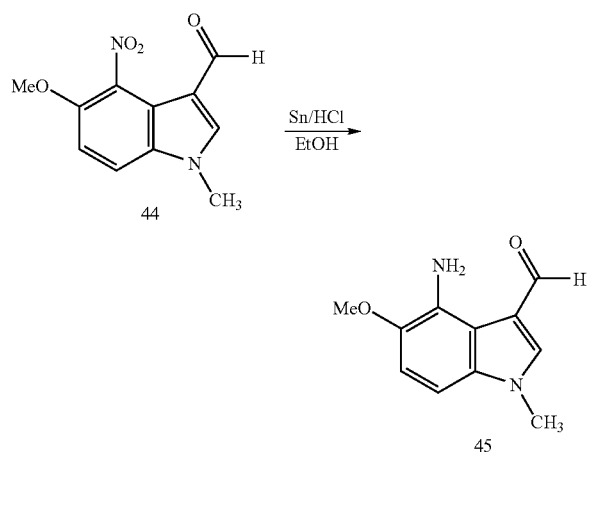

Tin powder (2.65 g, 22.3 mmol) was added to a suspension of nitroindole 44 (600 mg, 2.56 mmol) in EtOH (90 mL). Hydrochloric acid (3 M, 36 mL) was added and the mixture was stirred at room temperature for 2 h. The reaction mixture was decanted from the excess tin and added in portions to saturated sodium bicarbonate (200 mL). The mixture was extracted with EtOAc (4×) and the combined extracts were washed with sodium bicarbonate (1 M, 3×) and saturated NaCl (2×), dried (MgSO$_4$), filtered and evaporated. Compound 45 was isolated as a dark yellow oil (513 mg, 98%) and used in the following reaction without further purification; R$_f$=0.67 (EtOAc); $^1$H NMR (CDCl$_3$): δ 9.61 (s, 1H), 7.55 (s, 1H), 6.94 (d, 1H, J=8.6 Hz), 6.53 (d, 1H, J=8.6 Hz), 5.79 (bs, 2H), 3.88 (s, 3H), 3.76 (s, 3H).

d. 3-Formyl-5-methoxy-1-methylindole-4,7-dione (46)

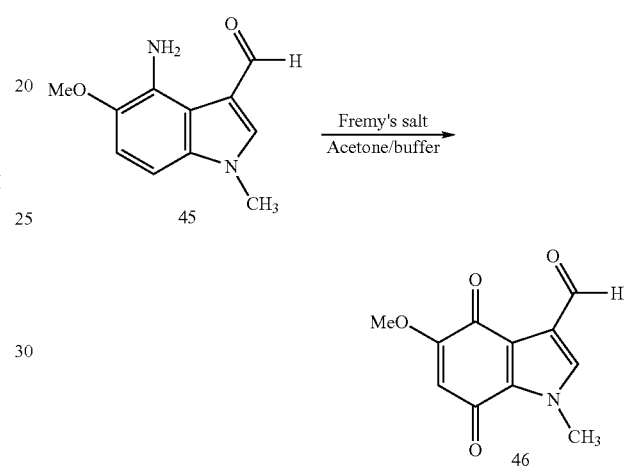

Potassium nitrosodisulfonate (1.85 g, 6.89 mmol) in H$_2$O (19 mL) was added to a solution of amine 45 (352 mg, 1.72 mmol) in acetone (37 mL). Sodium phosphate buffer (0.4 M, pH 6, 10 mL) was added and the reaction mixture was stirred at room temperature for 1.5 h. The acetone was removed under reduced pressure and the yellow solid was collected by filtration and washed with H$_2$O. The solid was taken up in warm EtOAc (100 mL) and a small amount of an insoluble solid was removed by filtration. The filtrate was rotovaped and the product was passed through a plug of silica gel (100:10:0.5 CHCl$_3$:EtOAc:MeOH) to afford 46 (310 mg, 82%) as a yellow solid; R$_f$=0.44 (100:10:0.5 CHCl$_3$:EtOAc:MeOH); $^1$H NMR (CDCl$_3$): δ 10.41 (s, 1H), 7.45 (s, 1H), 5.77 (s, 1H), 4.03 (s, 3H), 3.87 (s, 3H).

e. 3-Hydroxymethyl-5-methoxy-1-methylindole-4,7-dione (42)

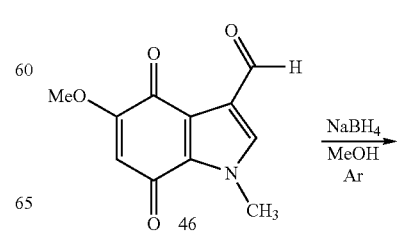

-continued

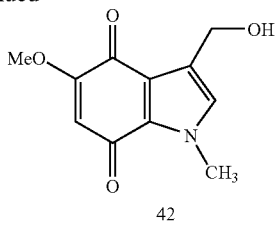

Aldehyde 46 (50 mg, 0.228 mmol) was added to anhydrous MeOH (30 mL) that had been degassed by bubbling with argon for 1.5 h. The suspension was degassed with argon for 15 min, NaBH$_4$ (65 mg, 1.71 mmol) was added and the reaction mixture was stirred for 2 h. A persistent light yellow color indicated that the solvent was thoroughly degassed and the hydroquinone had formed. The solution turned dark orange following air-oxidation to the quinone. The MeOH was removed under reduced pressure and the residue was taken up in CH$_2$Cl$_2$ (30 mL), washed with H$_2$O (2×) and saturated NaCl, dried (MgSO$_4$), filtered and evaporated. Column chromatography of the crude product (EtOAc) afforded 42 (24.2 mg, 48%) as a bright orange solid; R$_f$=0.57 (EtOAc); mp=182–184° C.; lit. mp=185–186° C.[53]; $^1$H NMR (CDCl$_3$): δ 6.71 (s, 1H), 5.69 (s, 1H), 464 (s, 2H), 3.94 (s, 3H), 3.85 (s, 3H).

EXAMPLE 12

3-(5-Methoxy-1-methyl-4,7-indolequinonyl)methyl N,N-bis(2-bromoethyl)phosphorodiamidate (4)

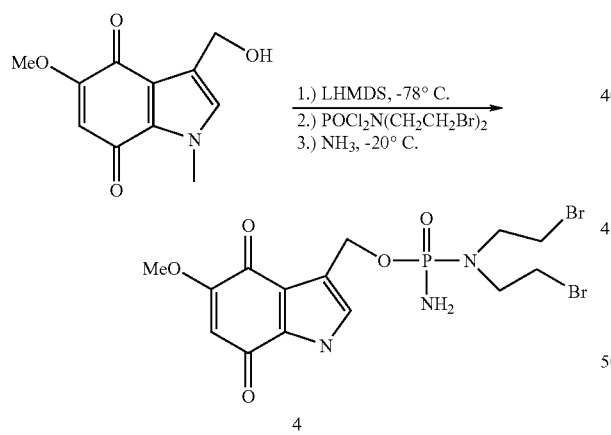

LHMDS (0.25 mL, 1.0M in THF) was added dropwise to a solution of 3-hydroxymethyl-5-methoxy-1-methylindole-4,7-dione 12 (50 mg, 0.23 mmol) in THF (10 mL). The solution was stirred for 10 min at −78° C. A solution of Cl$_2$P(O)N(CH$_2$CH$_2$Br)$_2$ (87 mg, 0.25 mmol) in THF (5 mL) was added all at once to the alkoxide, and the resulting solution was stirred for 1.5 h at −78° C. The solution was warmed to −20° C. and ammonia gas was bubbled through the reaction mixture for 6 min. The mixture was stirred for an additional 7 min and then added to CH$_2$Cl$_2$/H$_2$O and extracted (CH$_2$Cl$_2$, 3×). The combined organic layers were dried over Na$_2$SO$_4$ and evaporated. Column chromatography of the crude product (EtOAc/Acetone) afforded 4 (17.8 mg, 30% based on recovered starting material) as a yellow solid; R$_f$=0.47 (50% EtOAc/Acetone); $^1$H NMR (CDCl$_3$): δ 6.88 (1H, s), 5.71 (1H, s), 5.04 (2H, m), 3.96 (3H, s), 3.84 (3H, s), 3.47 (8H, m), 3.22 (2H, bs); $^{31}$P NMR (CDCl$_3$): 6–9.99 (Ref=TPPO); HPLC (40% CH$_3$CN/0.1% TFA H$_2$O): 6.97 min.

The intermediate compound 12 was prepared as follows.

a. 5-Methoxy-1-methylindole-2-carboxylic acid methyl ester (8):

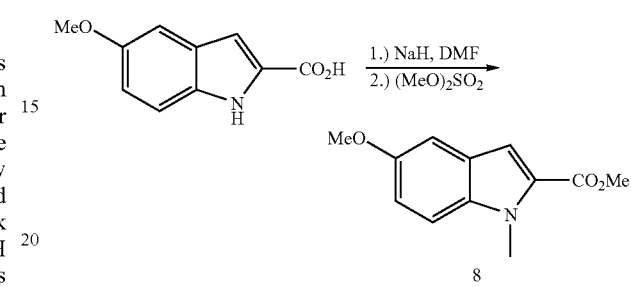

A solution of 5-methoxyindole-2-carboxylic acid (2.00g, 10.46 mmol) in anhydrous DMF (28 mL) was added to sodium hydride (1.68g, 41.84 mmol, 60% dispersion in mineral oil) at 0° C., under an argon atmosphere. The mixture was stirred for 5 min, dimethyl sulfate (2.96 mL, 31.38 mmol) was added, and the reaction was stirred at room temperature for 48 h. HCl (2M) was added and the resulting mixture extracted with CH$_2$Cl$_2$ (3×). The combined organic layers were dried over Na$_2$SO$_4$ and evaporated. Column chromatography of the crude product (25% EtOAc/Hexanes) afforded 8 (1.77 g, 78%) as an ivory solid; R$_f$=0.84 (25% EtOAc/hexanes); $^1$H NMR (CDCl$_3$): δ 7.33 (1H, s), 7.30 (1H, d), 7.20 (1H, s), 7.14 (1H, d), 4.05 (3H, s), 3.94 (3H, s), 3.90 (3H, s).

b. 5-Methoxy-1-methyl-4-nitroindole-2-carboxylic acid methyl ester (9)

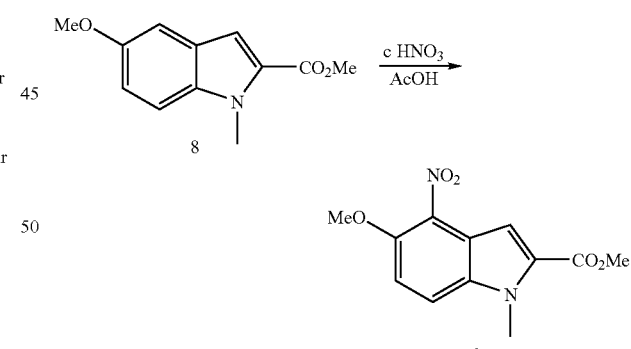

A solution of concentrated HNO$_3$ (2 mL) in AcOH (9 mL) was added to a solution of 8 (830 mg, 3.79 mmol) in AcOH (54 mL) at 0° C. Following the addition, the reaction mixture was warmed to room temperature and stirred for 2 h. The reaction mixture was poured over ice, filtered and the precipitate washed with H$_2$O. The precipitate was dissolved in CH$_2$Cl$_2$ and filtered through a short column of silica gel to afford 9 (780 mg, 78%) as a yellow solid; R$_f$=0.53 (50% EtOAc/hexanes); $^1$H NMR (CDCl$_3$): δ 7.58 (1H, d), 7.55 (1H, s), 7.18 (1H, d), 4.11 (3H, s), 4.02 (3H, s), 3.94 (3H, s).

c. 4-Amino-5-methoxy-1-methylindole-2-carboxylic acid methyl ester (10):

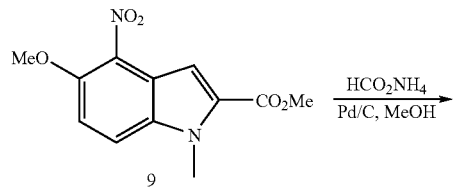

To a solution of 9 (1.0g, 3.78 mmol) in anhydrous methanol (90 mL) was added 10% Pd/C (150 mg) suspended in anhydrous methanol (15 mL) followed by ammonium formate (1.10 g, 17.4 mmol). The reaction mixture was stirred for 1 h, filtered through celite and the methanol removed. The residue was taken up in $CH_2Cl_2/H_2O$ and extracted with $CH_2Cl_2$ (3×). The combined organic layers were dried over $Na_2SO_4$ and evaporated to afford 10 (595 mg, 67%) as a brown solid which was used without further purification; $^1H$ NMR ($CDCl_3$): δ 7.21 (1H, s), 7.06 (1H, d), 6.72 (1H, d), 4.01 (3H, s), 3.90 (3H, s), 3.88 (3H, s).

d. 4-Amino-2-hydroxymethyl-5-methoxy-1-methylindole (11)

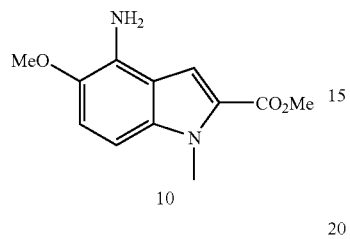

Lithium aluminum hydride (5.84 mL, 5.84 mmol, 1.0 M solution in $Et_2O$) was added to a solution of 10 (595 mg, 2.59 mmol) in THF (12 mL) under argon. The reaction was then heated at reflux for 15 min, quenched by careful addition of $H_2O$ followed by 1 M NaOH, then extracted with $CH_2Cl_2$ (3×). The combined organic layers were dried over $Na_2SO_4$ and evaporated to afford 11 (490 mg, 94%) as a brown oil which was used without further purification; $^1H$ NMR ($CDCl_3$): δ 6.95 (1H, d), 6.71 (1H, d), 6.34 (1H, s), 4.77 (2H, s), 3.87 (3H, s), 3.74 (3H, s).

e. 2-Hydroxymethyl-5-methoxy-1-methylindole-4,7-dione (12)

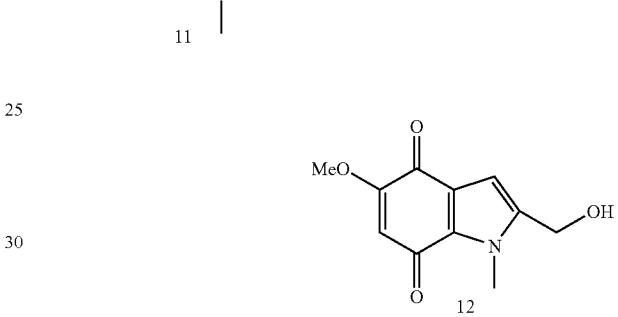

A solution of potassium nitrosodisulfonate $(KSO_3)_2NO$ (590 mg, 2.2 mmol) in sodium phosphate buffer (0.4 M, pH=6, 13 mL) was added to a solution of 11 (130 mg, 0.63 mmol) in acetone (8 mL). The reaction mixture was stirred for 1 h at room temperature, ethyl acetate and water were added, and the aqueous layer was extracted (EtOAc, 3×). The combined organic layers were dried over $Na_2SO_4$ and evaporated. Column chromatography of the crude product (EtOAc) afforded 12 (122 mg, 87%) as an orange solid; $R_f$=0.62 (EtOAc); $^1H$ NMR ($CDCl_3$): δ 6.58 (1H, s), 5.67 (1H, s), 4.68 (2H, s), 4.03 (3H, s), 3.83 (3H, s).

EXAMPLE 13

2-(5-Methoxy-1-methyl-4,7-indolequinonyl)methyl bis[N-methyl-N-(2-bromoethyl)]phosphorodiamidate (5):

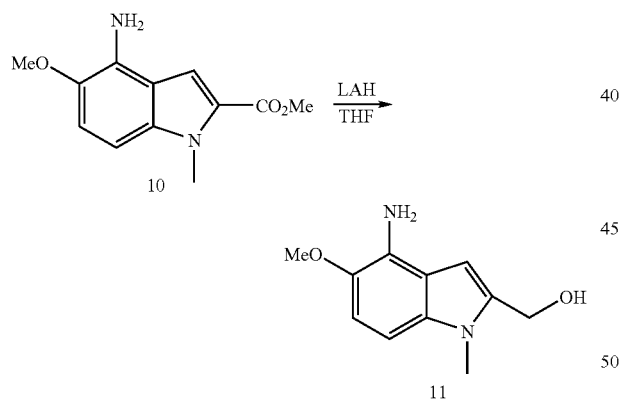

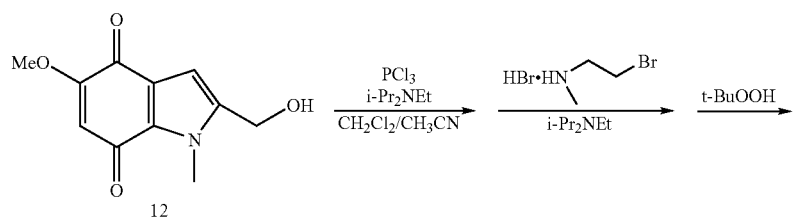

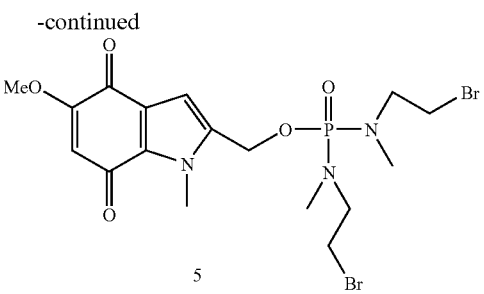

PCl₃ (0.12 ml, 2.0 M in CH₂Cl₂) was added dropwise to a solution of 12 (50 mg, 0.23 mmol) in CH₂Cl₂ (3 mL) and CH₃CN (2 mL) at −78° C., followed by the dropwise addition of i-Pr₂NEt (0.04 mL, 0.23 mmol). The reaction was stirred under argon at −78° C. After 15 min, methyl-bromoethylamine hydrobromide (99 mg, 0.46 mmol) in CH₃CN (1.5 mL) was added, followed by the dropwise addition of i-Pr₂NEt (0.16 mL, 0.92 mmol). The mixture was stirred for 2 h, t-BuOOH (0.12 mL, 5–6M in decane) was added, and the reaction mixture was warmed to −20° C. and stirred for 1 h. Water (3 mL) was added and the mixture was extracted with CH₂Cl₂ (3×). The combined organic extracts were washed with water, dried over Na₂SO₄, and concentrated. Reverse phase column column chromatography (45% MeOH/H₂O) afforded 5 (2.4 mg, 2%) as a yellow solid; $R_f$=0.33 (5% MeOH/EtOAc); ¹H NMR (CDCl₃): δ 6.69 (1H, s), 5.71 (1H, s), 5.03 (2H, d), 4.03 (3H, s), 3.84 (3H, s), 3.40 (8H, m), 2.70 (3H, s), 2.66 (3H, s); ³¹P NMR (CDCl₃): δ−10.01 (Ref=TPPO); HPLC (40% CH₃CN/0.1% TFA H₂O): 12.73 min; FAB MS: Calcd. for: 539.9898 found 539.9904.

Scheme for Examples 14 and 15

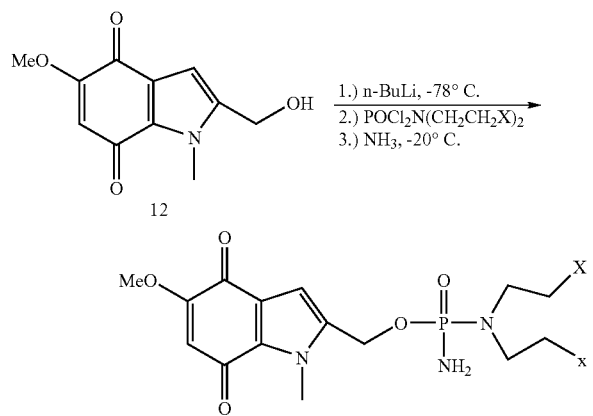

6a: X = Cl
6b: X = Br

EXAMPLE 14

2-(5-Methoxy-1-methyl-4,7-indolequinonyl)methyl N,N-bis(2-chloroethyl)phosphorodiamidate (6a)

n-Butyllithium (0.05 mL, 2.5M in hexanes) was added dropwise to a solution of 12 (25 mg, 0.11 mmol) in THF (3 mL). The solution was allowed to stir for 10 min at −78° C., and a solution of Cl₂P(O)N(CH₂CH₂Cl)₂ (34 mg, 0.13 mmol) in THF (0.5 mL) was added all at once. The solution was stirred for 1.5 h at −78° C. then warmed to −20° C. and ammonia gas was bubbled through the reaction mixture for 7 min. The reaction was stirred for an additional 8 min and then added to CH₂Cl₂/H₂O and extracted (3×). The combined organic layers were dried over Na₂SO₄ and evaporated. Column chromatography of the crude product (20% EtOAc/Acetone) afforded 6a (27.6 mg, 59%) as a golden solid; $R_f$=0.47 (20% EtOAc/Acetone); ¹H NMR (CDCl₃): δ 6.68 (1H, s), 5.69 (1H, s), 5.01 (2H, m), 4.02 (3H, s), 3.83 (3H, s), 3.65 (4H, m), 3.47 (4H, m), 2.03 (2H, bs); ³¹P NMR (CDCl₃): δ−9.35 (Ref=TPPO); HPLC (40% CH₃CN/0.1% TFA H₂O): 5.93 min; FAB MS: Calcd. for: 446.0415 found 446.0419.

EXAMPLE 15

2-(5-Methoxy-1-methyl-4,7-indolequinonyl)methyl N,N-bis(2-bromoethyl)phosphorodiamidate (6b)

The title compound was prepared on a 0.11 mmol scale as described above for 6a, except that Cl₂P(O)N(CH₂CH₂Br)₂ was used as the phosphorylating agent. Column chromatography of the crude product (30% EtOAc/Acetone) afforded 6b (33.8 mg, 60%) as a peach solid; $R_f$=0.53 (30% EtOAc/Acetone); ¹H NMR (CDCl₃): δ 6.69 (1H, s), 5.70 (1H, s), 5.05 (2H, d), 4.02 (3H, s), 3.83 (3H, s), 3.473 (8H, m), 2.90 (2H, bs); ³¹P NMR (CDCl₃): δ−9.66 (Ref=TPPO); HPLC (40% CH₃CN/0.1% TFA H₂O): 7.02 min; FAB MS: Calcd. for: 511.9585 found 511.9579. Anal. Calcd. for C₁₅H₂₀Br₂N₃O₅P: C 35.11 H 3.93 N 8.19 found C 35.33 H 4.02 N 7.82.

EXAMPLE 16

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |

| -continued | |
|---|---|
| Sodium starch glycolate | 15.0 |
| Magnesium stearate | 5.0 |
| | 500.0 |
| (iii) Capsule | mg/capsule |
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |
| (iv) Injection 1 (1 mg/ml) | mg/ml |
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |
| (v) Injection 2 (10 mg/ml) | mg/ml |
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound a compound of formula I:

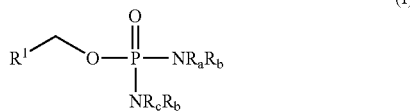

(I)

wherein:
R$^1$ is an organic releasing group comprising a quinone ring;
R$_a$, R$_b$, R$_c$, and R$_d$ are each independently hydrogen, (C$_1$–C$_6$)alkyl, or —CH$_2$CH$_2$X; and
each X is independently halo, (C$_1$–C$_6$)alkylsulfonyl, halo (C$_1$–C$_6$)alkylsulfonyl, or arylsulfonyl, wherein each aryl is optionally substituted with one or more (e.g. 1, 2, 3, or 4) halo, (C$_1$–C$_6$)alkyl, halo(C$_1$–C$_6$)alkyl, (C$_1$–C$_6$)alkoxy, (C$_1$–C$_6$)alkanoyl, (C$_1$–C$_6$)alkanoyloxy, (C$_1$–C$_6$)alkoxycarbonyl, cyano, nitro, or trifluoromethoxy;
provided at least two of R$_a$, R$_b$, R$_c$, and R$_d$ are —CH$_2$CH$_2$X;
or a pharmaceutically acceptable salt thereof.

2. The compound of claim 1 wherein R$^1$ is a group of formula (II):

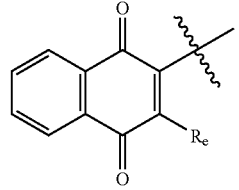

(II)

wherein R$_c$ is hydrogen, halo, (C$_1$–C$_6$)alkyl, halo(C$_1$–C$_6$) alkyl, (C$_1$–C$_6$)alkoxy, (C$_1$–C$_6$)alkanoyloxy, cyano, nitro, or (C$_1$–C$_6$)alkylthio; and
wherein the benz ring is optionally substituted by one or more (e.g. 1, 2, 3, or 4) hydroxy, halo, (C$_1$–C$_6$)alkyl, halo(C$_1$–C$_6$)alkyl, (C$_1$–C$_6$)alkoxy, (C$_1$–C$_6$)alkylthio; (C$_1$–C$_6$)alkanoyl, (C$_1$–C$_6$)alkanoyloxy, (C$_1$–C$_6$)alkoxycarbonyl, cyano, nitro, mercapto, trifluoromethoxy, or NR$_f$R$_g$;
wherein each R$_f$ and R$_g$ is independently hydrogen, (C$_1$–C$_6$) alkyl, (C$_1$–C$_6$)alkanoyl, phenyl, benzyl, or phenethyl; or R$_f$ and R$_g$ together with the nitrogen to which they are attached are pyrrolidino, piperidino or morpholino.

3. The compound of claim 1 wherein X is bromo, chloro, mesyl, trifluoromethylsulfonyl, or tosyl.

4. The compound of claim 1 wherein X is bromo.

5. The compound of claim 2 wherein R$_c$ is hydrogen, halo, methyl, or methylthio.

6. The compound of claim 1 wherein R$_a$ is (C$_1$–C$_6$)alkyl.

7. The compound of claim 1 wherein R$_c$ is (C$_1$–C$_6$)alkyl.

8. The compound of claim 1 wherein R$_a$ and R$_b$ are each independently —CH$_2$CH$_2$X.

9. The compound of claim 1 wherein R$_c$, and R$_d$ are each independently —CH$_2$CH$_2$X.

10. The compound of claim 1 wherein R$_b$ and R$_d$ are each independently —CH$_2$CH$_2$X.

11. The compound of claim 1 wherein R$_a$ is methyl.

12. The compound of claim 1 wherein R$_c$ is methyl.

13. The compound of claim 1 wherein R$_a$ and R$_b$ are each —CH$_2$CH$_2$Br.

14. The compound of claim 1 wherein R$_c$, and R$_d$ are each —CH$_2$CH$_2$Br.

15. The compound of claim 1 wherein R$_b$ and R$_d$ are each —CH$_2$CH$_2$Br.

16. The compound of claim 1 wherein R$_a$ and R$_b$ are each independently —CH$_2$CH$_2$Cl.

17. The compound of claim 1 wherein R$_c$, and R$_d$ are each independently —CH$_2$CH$_2$Cl.

18. The compound of claim 1 wherein R$_b$ and R$_d$ are each independently —CH$_2$CH$_2$Cl.

19. The compound of claim 1 which is:
2-(1,4-naphthoquinonyl)methyl N,N-bis(2-chloroethyl) phosphorodiamidate;
2-(3-methyl-1,4-naphthoquinonyl)methyl N,N-bis(2-chloroethyl) phosphorodiamidate;
2-(3-thiomethyl-1,4-naphthoquinonyl)methyl N,N-bis(2-chloroethyl) phosphorodiamidate;
2-(3-bromo-1,4-naphthoquinonyl)methyl N,N-bis(2-chloroethyl) phosphorodiamidate;
2-(1,4-naphthoquinonyl)methyl N,N-bis(2-bromoethyl) phosphorodiamidate;
2-(3-methyl-1,4-naphthoquinonyl)methyl N,N-bis(2-bromoethyl) phosphorodiamidate;
2-(1,4-naphthoquinonyl)methyl bis[N-(2-chloroethyl)] phosphorodiamidate;
2-(1,4-naphthoquinonyl)methyl bis[N-methyl-N-(2-bromoethyl)]phosphorodiamidate;

2-(3-methyl-1,4-naphthoquinonyl)methyl bis[N-methyl-N-(2-bromo ethyl)]phosphorodiamidate;

2-(1,4-naphthoquinonyl)methyl bis[N-methyl-N-(2-chloroethyl)] phosphorodiamidate; or a pharmaceutically acceptable salt thereof.

20. A pharmaceutical composition comprising a compound of claim 1, in combination with a pharmaceutically acceptable diluent or carrier.

21. A method for preparing a compound of formula I as described in claim 1, wherein $R^1$ is a group of formula II

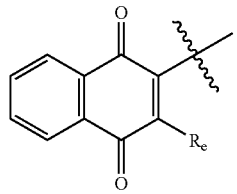

(II)

comprising oxidizing a corresponding compound of formula I wherein $R^1$ is a group of formula VI

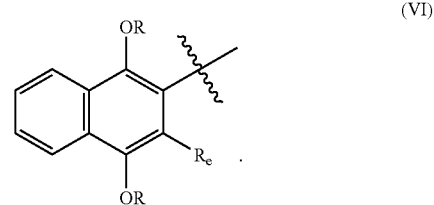

(VI)

22. The compound of claim 1, wherein the organic releasing group is capable of releasing a group of formula —O—P(=O)(NR$_a$R$_b$)(NR$_c$R$_d$) in vivo from the compound of formula I.

* * * * *

UNITED STATES PATENT AND TRADEMARK OFFICE
CERTIFICATE OF CORRECTION

PATENT NO. : 7,304,046 B2  
APPLICATION NO. : 10/725,191  
DATED : December 4, 2007  
INVENTOR(S) : Richard F. Borch, Marcy Hernick and Carolee Flader Page 1 of 1

It is certified that error appears in the above-identified patent and that said Letters Patent is hereby corrected as shown below:

Column 37, line 41 delete the text "a compound"

Signed and Sealed this

Fifteenth Day of April, 2008

JON W. DUDAS  
*Director of the United States Patent and Trademark Office*